United States Patent
Fourt et al.

(10) Patent No.: US 9,872,961 B2
(45) Date of Patent: Jan. 23, 2018

(54) AUTOMATIC INJECTION DEVICE WITH TRIGGER ASSEMBLY

(71) Applicant: Eli Lilly and Company, Indianapolis, IN (US)

(72) Inventors: Jesse Arnold Fourt, Menlo Park, CA (US); Jennifer Ellen Davis-Wilson, Mountain View, CA (US); Bradley Simpson, Palo Alto, CA (US); James R. Yurchenco, Palo Alto, CA (US)

(73) Assignee: Eli Lilly and Company, Indianapolis, IN (US)

( * ) Notice: Subject to any disclaimer, the term of this patent is extended or adjusted under 35 U.S.C. 154(b) by 471 days.

(21) Appl. No.: 14/435,765

(22) PCT Filed: Oct. 11, 2013

(86) PCT No.: PCT/US2013/064476
§ 371 (c)(1),
(2) Date: Apr. 15, 2015

(87) PCT Pub. No.: WO2014/062488
PCT Pub. Date: Apr. 24, 2014

(65) Prior Publication Data
US 2015/0246181 A1  Sep. 3, 2015

Related U.S. Application Data

(60) Provisional application No. 61/716,029, filed on Oct. 19, 2012.

(51) Int. Cl.
*A61M 5/315* (2006.01)
*A61M 5/20* (2006.01)
(Continued)

(52) U.S. Cl.
CPC ...... *A61M 5/31566* (2013.01); *A61M 5/2033* (2013.01); *A61M 5/3158* (2013.01);
(Continued)

(58) Field of Classification Search
CPC ............ A61M 5/31566; A61M 5/2033; A61M 5/3158; A61M 5/3202; A61M 5/326;
(Continued)

(56) References Cited

U.S. PATENT DOCUMENTS

| 8,052,653 B2 | 11/2011 | Gratwohl et al. |
| 8,167,840 B2 | 5/2012 | Matusch |

(Continued)

FOREIGN PATENT DOCUMENTS

| WO | 2003097133 | 11/2003 |
| WO | 2007002052 | 1/2007 |

(Continued)

OTHER PUBLICATIONS

Patent Cooperation Treaty International Search Report and Written Opinion of the International Searching Authority pertaining to International Application No. PCT/US2013/064476, dated Feb. 5, 2014.

*Primary Examiner* — Manuel Mendez
(74) *Attorney, Agent, or Firm* — M. Daniel Spillman

(57) ABSTRACT

Automatic injection device with trigger assembly. The trigger assembly includes a button (25), and a single prong (160) extending from a biased element of the device toward the button. A button-engaging surface (167) of the prong and a support surface of the device define a radially extending opening in which an actuating element (52) of the button fits for a radially outward face of the actuating element to be backed up by the support surface. For release of the biased element, when the button is pressed to shift the actuating element to cause a latching surface of the prong to disengage from a latch surface of the device, motion of the actuating element in a direction away from the prong is limited by the radially outward face of the actuating element abutting the support surface.

8 Claims, 51 Drawing Sheets

(51) Int. Cl.
*A61M 5/32* (2006.01)
*A61M 5/31* (2006.01)

(52) U.S. Cl.
CPC ........... *A61M 5/3202* (2013.01); *A61M 5/326* (2013.01); *A61M 2005/206* (2013.01); *A61M 2005/2073* (2013.01); *A61M 2005/3143* (2013.01); *A61M 2205/583* (2013.01)

(58) Field of Classification Search
CPC .... A61M 2005/206; A61M 2005/2073; A61M 2005/3143; A61M 2205/583
USPC ....................................................... 604/196
See application file for complete search history.

(56) References Cited

U.S. PATENT DOCUMENTS

| | | |
|---|---|---|
| 2009/0124981 A1 | 5/2009 | Evans |
| 2010/0100040 A1 | 4/2010 | Matusch |
| 2010/0217105 A1 | 8/2010 | Yodfat et al. |
| 2011/0034878 A1 | 2/2011 | Radmer et al. |
| 2012/0197186 A1 | 8/2012 | Matusch |

FOREIGN PATENT DOCUMENTS

| | | |
|---|---|---|
| WO | 2008112472 | 9/2008 |
| WO | 2009092807 | 7/2009 |
| WO | 2011048422 | 4/2011 |
| WO | 2011109205 | 9/2011 |
| WO | 20120049468 | 4/2012 |

AUTOMATIC INJECTION DEVICE WITH TRIGGER ASSEMBLY

BACKGROUND OF THE INVENTION

The present invention pertains to pharmaceutical injection devices, and, in particular, to a trigger assembly within an automatic injection device.

Patients suffering from a number of different diseases frequently must inject themselves with pharmaceuticals. A variety of devices have been proposed to facilitate these injections. One type of device is an automatic injection device. This type of device typically includes a trigger assembly that when operated by a user causes the device to automatically insert into the user a needle of a syringe that prior to triggering was disposed within the device housing, and then the device automatically injects a dose of medication through that inserted needle.

One shortcoming with some trigger assemblies relates to the way the trigger feels to the user. For instance, the triggering experience for a given type of device varies from device to device. This variance may be present in devices in which the triggering mechanism uses multiple prongs intended to be released at the same time to trigger operation, but due to, for example, manufacturing variability the prongs release in stages that are noticeable to a user. In some cases, operation of a trigger assembly requires a large spring force be overcome. For example, in some devices the spring force that in essence opposes the trigger operation also is used to directly drive the syringe plunger. With increasing diameter plungers, or in situations where the medication being acted upon by the plunger is more viscous, larger spring forces are required, which therefore can impact the triggering of those devices. Because injection devices are often made of plastic parts so as to be economical to manufacture, overcoming large spring forces can result in a trigger part deforming when in use. This deforming may compromise the efficiency of the trigger operation and make it more difficult for a person to operate the trigger. And, making trigger assemblies bigger or out of relatively expensive materials so as to better accommodate larger operational forces may not be an option due to cost or space constraints within a suitably sized automatic injection device.

Thus, it would be desirable to provide a trigger assembly for an automatic injection device which can overcome one or more of these and other shortcomings of the prior art.

BRIEF SUMMARY OF THE INVENTION

In one form thereof, the present invention provides a trigger assembly for an automatic injection device. The trigger assembly by its operation releases a biased element of the device for movement in a first axial direction relative to a housing of the device. The trigger assembly includes a button shiftable relative to the housing from a first axial position to a second axial position. The button includes an actuating element extending in a first axial direction and including a radially inward face and a radially outward face. The radially inward face includes a prong-engaging surface. The trigger assembly includes a single prong extending from the biased element toward the button and includes at least one latching surface and a button-engaging surface for sliding engagement with the prong-engaging surface of the actuating element. At least one of the prong-engaging surface and the button-engaging surface is angled relative to the axial direction to provide a ramp. The button-engaging surface and a support surface of the device define a radially extending opening in which the actuating element fits for the radially outward face of the actuating element to be backed up by the support surface. The actuating element and the single prong are structured and arranged such that when the button is in the first axial position, the at least one latching surface is in a radial position at which an at least one latch surface of the device is engagable to prevent movement of the biased element in the first axial direction, and such that movement of the button from the first axial position to the second axial position shifts the at least one latching surface radially for disengagement from the at least one latch surface, whereby motion of the actuating element in a direction away from the prong is limited by the radially outward face of the actuating element abutting the support surface.

One advantage of the present invention is that a trigger assembly for an automatic injection device may be provided which allows for a convenient operation by a user, and which trigger assembly, from device to device, is readily repeatable in production so that it provides a consistent experience for users of the type of injection device in which it is employed.

Another advantage of the present invention is that a trigger assembly for an automatic injection device may be provided which is suitably robust without being overly large or costly.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
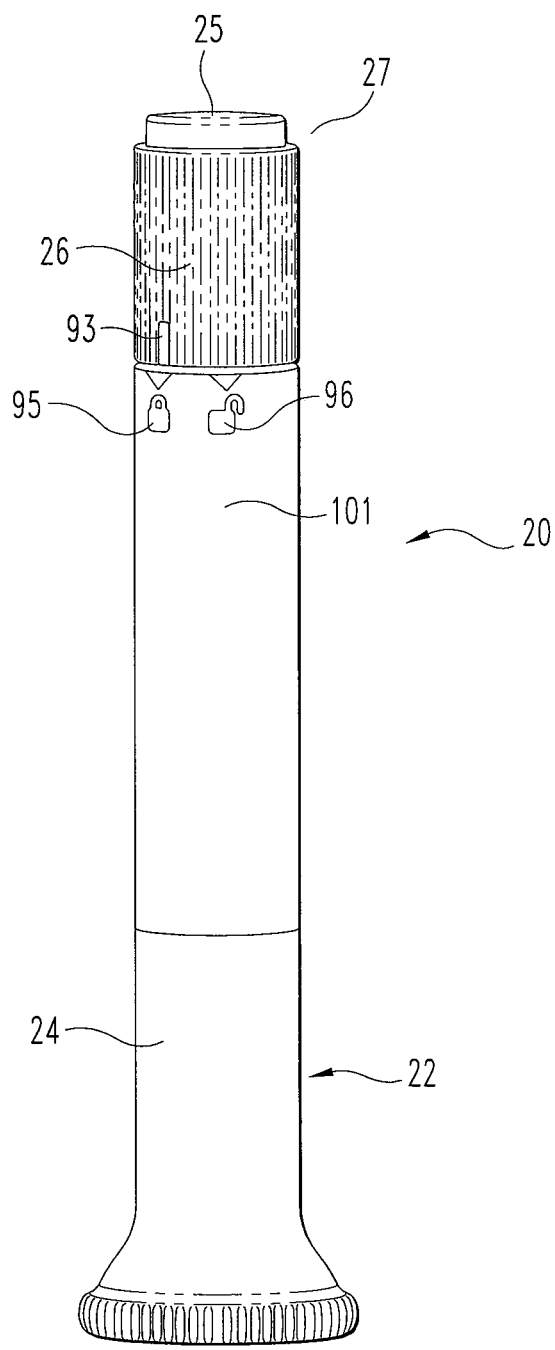
FIG. 1 is a side view of an automatic injection device with a trigger assembly of the present invention, which device is shown in a locked arrangement prior to use.

Corresponding reference characters indicate corresponding parts throughout the several views. Although the drawings represent embodiments of the present inventions, the drawings are not necessarily to scale, and certain features may be exaggerated or omitted in some of the drawings in order to better illustrate and explain the present invention.

DETAILED DESCRIPTION OF THE INVENTION

Figure 2:
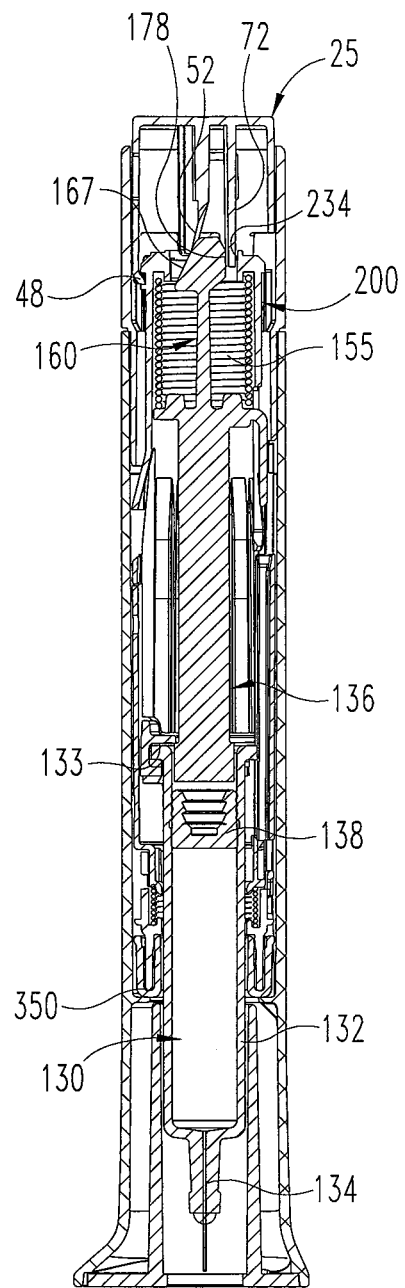
FIG. 2 is a longitudinal cross-sectional view of the automatic injection device of FIG. 1 with the overcap removed.
Figure 3A:
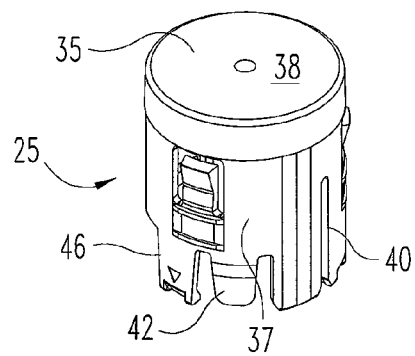
FIGS. 3a, 3b, 3c, 3d, 3e, 3f and 3g are respectively perspective, bottom, first side, first longitudinal cross-sectional, transverse cross-sectional, second side and second longitudinal cross-sectional views of a button shown separate from the other components of the device of FIG. 1.
Figure 3B:
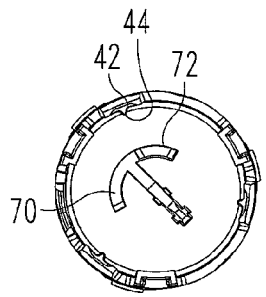
Figure 3C:
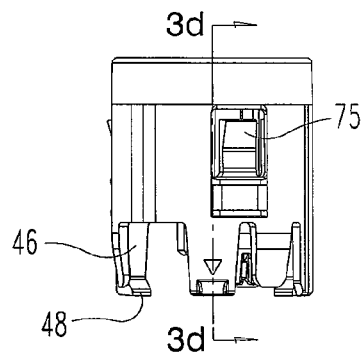
Figure 3D:
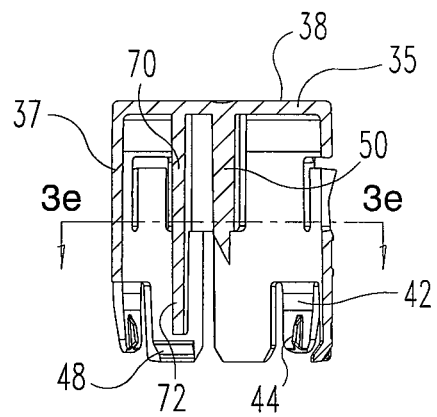
Figure 3E:
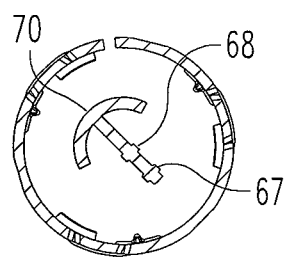
Figure 3F:
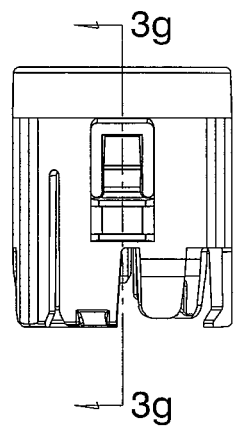
Figure 3G:
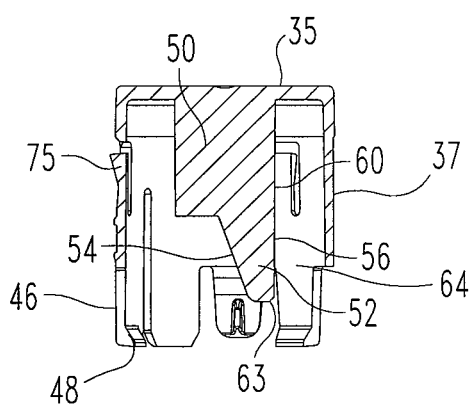
Figure 4A:
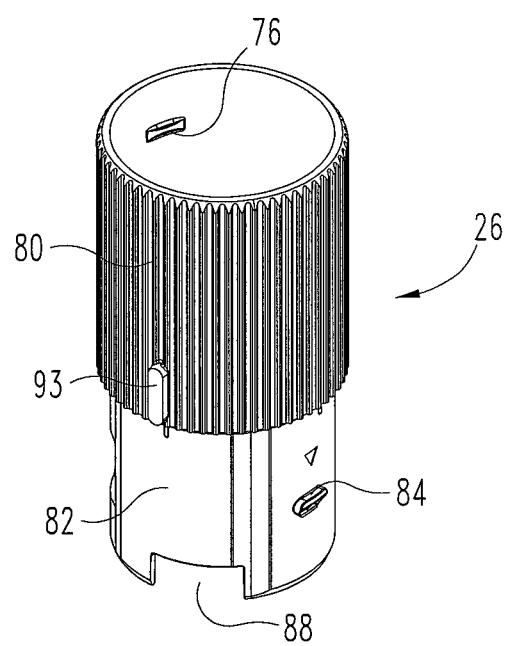
FIGS. 4a, 4b, 4c, 4d and 4e are respectively perspective, first side, first longitudinal cross-sectional, second side and second longitudinal cross-sectional views of a housing safety sleeve shown separate from the other device components.
Figure 4B:
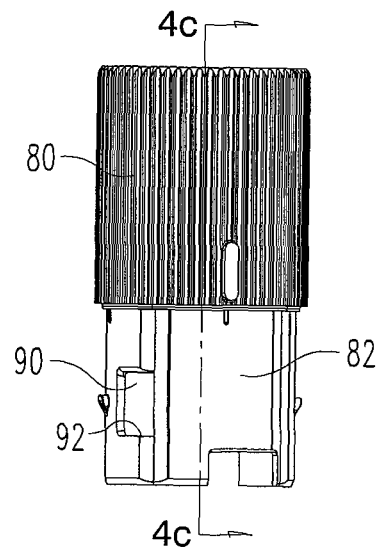
Figure 4C:
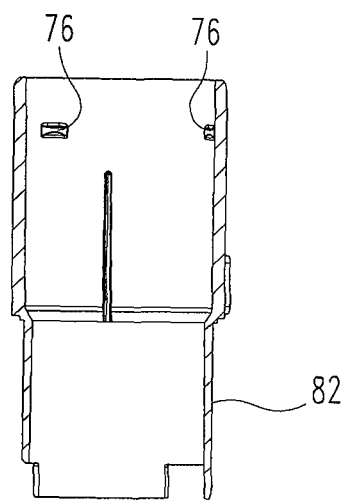
Figure 4D:
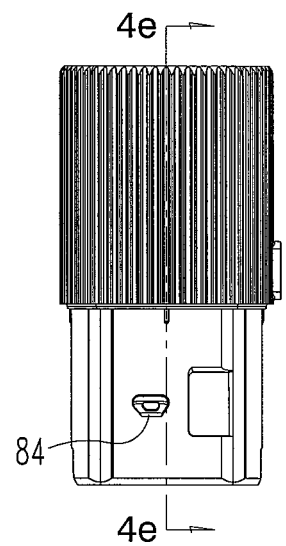
Figure 4E:
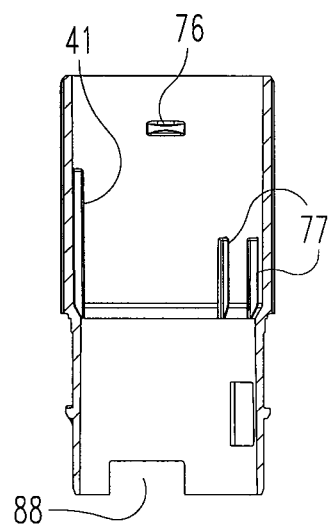
Figure 5A:
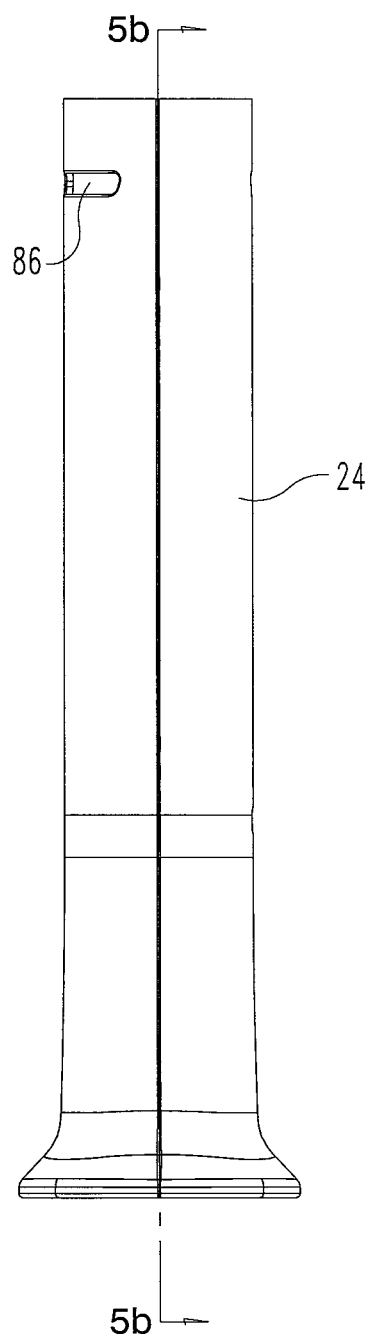
FIGS. 5a, 5b, 5c and 5d are respectively first side, first longitudinal cross-sectional, second side and second longitudinal cross-sectional views of a the housing main body shown separate from the other device components.
Figure 5B:
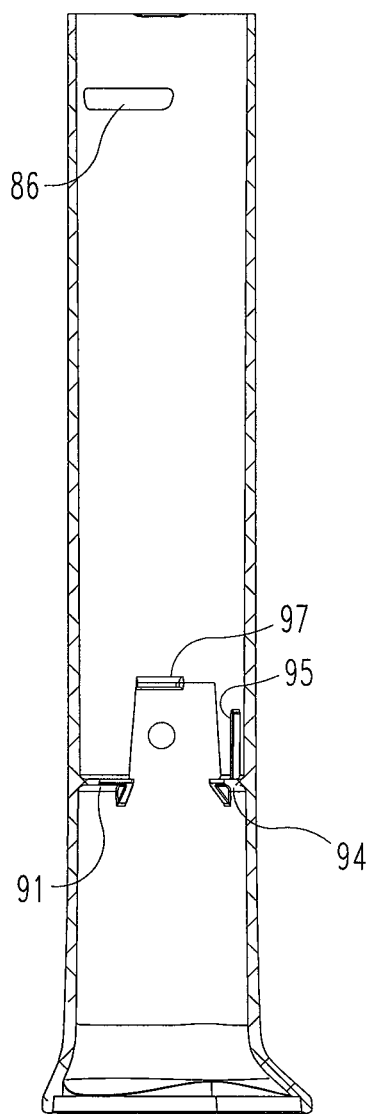
Figure 5C:
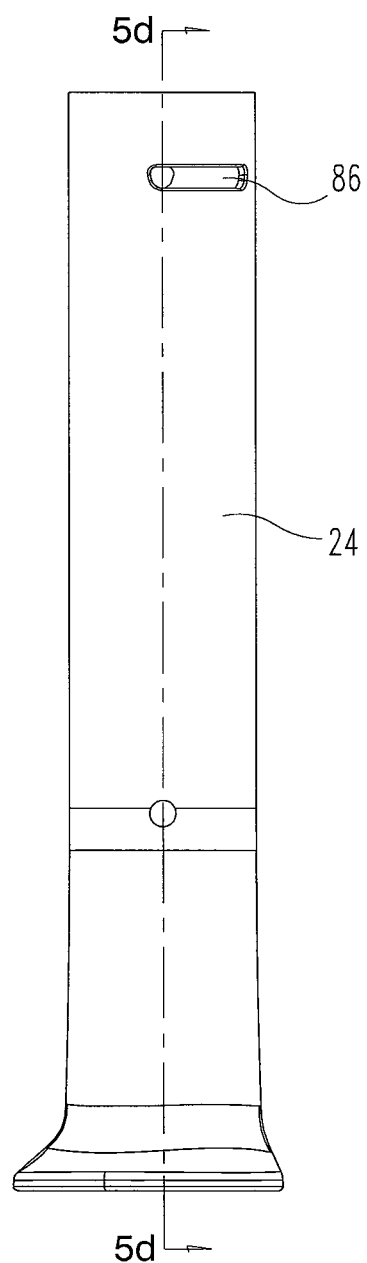
Figure 5D:
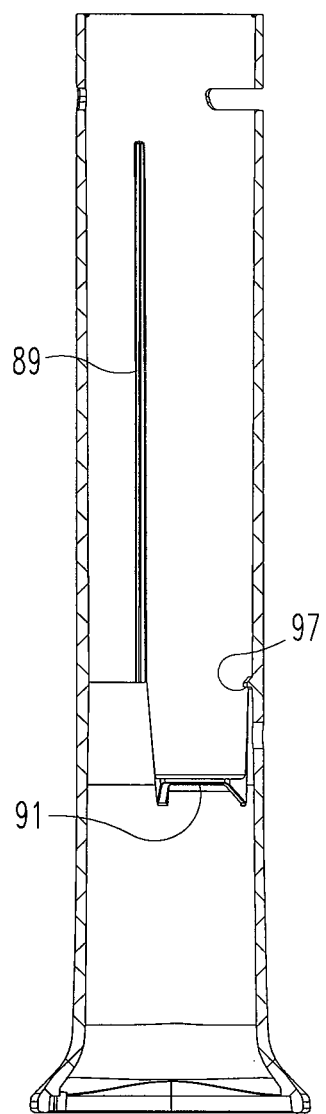

Referring now to FIGS. 1 and 2, there are shown different views of a first embodiment of an automatic injection device, generally designated 20, with a trigger assembly of the present invention. When the inventive trigger assembly is operated, the needled syringe of the device 20 is automatically driven downward such that the injection needle projects beyond the bottom end of the device housing to penetrate the user. The device then proceeds to inject automatically, that is without further user action, the medication contents of the syringe through the needle, after which the syringe is retracted automatically such that the needle is returned to within the housing.

Although the inventive trigger assembly is shown finding beneficial application in the device 20 described herein, such application is merely illustrative and not intended to be limiting. The inventive trigger assembly can be used in many different types of automatic injection devices where its benefits are desired, including devices in which the insertion of the needle is manually performed but the forcing of the medicine through the needle is automatic once triggered, as well as devices where the injection refers to the automatic insertion of the needle but the forcing of medicine through the needle is manually powered.

It will be appreciated from the following description that device 20 is conceptually similar in various aspects to the devices disclosed in International Publication Number WO 2011/109205, which publication is incorporated herein in its entirety.

Device 20 includes an outer housing 22 in which are operationally disposed working components of the device. The outer housing 22 includes a safety sleeve 26 and a main body 24 that together form the axial height of the outer housing. Safety sleeve 26 is rotatable relative to main body 24 by the user. A button 25 that is part of the trigger assembly protrudes in the axial direction from the top or distal end 27 of the housing. When properly rotationally oriented by rotation of sleeve 26, button 25 is unlocked such that it can be depressed in the proximal direction to start the automatic injection function of device 20. As used herein, distal and proximal refer to axial locations relative to an injection site when the device is oriented for use at such site, whereby, for example, proximal end of the housing refers to the housing end that is closest to such injection site.

Button 25 is molded as a single piece from a suitably durable material, such as Lustran ABS 348. As further shown in FIGS. 3a-3g, button 25 includes an end disc 35 with a skirt 37 extending proximally from the outer periphery of disc 35. End disc 35 has a flat distal face 38 upon which a force can be directly applied by a user to selectively plunge the button to trigger the device. A notch 40 formed in skirt 37 at its proximal end extends axially and forms a slot which receives rib 41 of housing sleeve 26 so as to rotatably key together the button 25 and sleeve 26. A set of three equally angularly spaced resilient fingers 42 each provided with a detent bump 44 on its radially inward face are provided at the base of skirt 37 for locating the button 25 on shuttle 200. Each finger 42 is adjacent to one of three equally angularly spaced fingers 46 with inwardly angled stops 48 also provided in skirt 37 for attachment to shuttle 200.

Depending from the underside of disc 35 is a rigid, bar shaped flange including a rectangular portion 50 and a tapered portion 52 located below the rectangular portion. As further shown in FIG. 17, a first set of strengthening ribs 67 longitudinally extend along both sides of flange portions 50 and 52 near their radial outermost extent, and a second set of strengthening ribs 68 longitudinally extend along both sides of flange portion 50 inward of ribs 67.

Flange tapered portion 52 includes a radially inward surface 54 that is sloped relative to the axial direction to form a ramp. The radially outward surface 56 of flange portion 52 extends axially and is aligned with the outer edge 60 of flange portion 50. Surface 54 and surface 56 converge at a rounded tip 63 of flange portion 52. The space or gap 64 between flange surface 56 and button skirt 37 is opened at the bottom and accommodates a rigid section of the shuttle. Tapered flange portion 52 with its sloped surface 54 serves as an actuating element of the trigger which cams a prong of the trigger to unlatch it for the shown trigger assembly. Differently designed actuating elements, including one that is not ramp shaped, can be used to cam and thereby unlatch the prong in alternate embodiments.

A rigid flange 70 that depends from the underside of disc 35 is arcuate in shape. Rectangular flange portion 50 tees into rigid flange 70 for additional strength. A safety arm 72 axially extends in the proximal direction from one end region of flange 70. Arm 72 serves to back up the trigger prong when the device is in a locked state to prevent inadvertent trigger activation caused by, for example, a jarring force on the device caused by it being accidentally dropped.

Skirt 37 is formed with three openings therethrough that define three resilient snaps 75 that engage bumps 76 on sleeve 26 to axially secure the button 25 relative to sleeve 26 after button plunging.

Housing sleeve 26 is further shown in FIGS. 4a-4e and is made of plastic material with a grippable main body portion 80. A reduced diameter portion 82 of sleeve 26 fits within housing main body 24 and includes two snaps 84 evenly spaced around the circumference that fit within slots 86 in main body 24. Snaps 84 and slots 86 allow rotational motion, but prevent axial motion, between sleeve 26 and main body 24. An opening 90 forms a lock ledge 92 for shuttle capture.

Two notches 88 are formed in the proximal edge of sleeve portion 82. One notch 88 accommodates the distal end of housing key 89 to limit the angular positions of sleeve 26 relative to main body 24. At these angular positions of housing sleeve 26, indicator 93 on sleeve 26 aligns with either lock icon 95 or unlock icon 96 shown in FIG. 1 to provide a visual notice to a user of the lock status of the device. Icons 95 and 96 are marked on a label 101 that is adhesively attached around housing main body 24.

A series of three longitudinally extending ribs 77 that are angularly spaced jut inward within sleeve 26. When button 25 is plunged to activate device 20, that plunging in the proximal direction is halted by the button bottoming out on the tops of ribs 77, as well as rib 41 abutting skirt 37 at the top of notch 40. Ribs 77 as well as rib 41 also radially, or transverse to the axial direction, locate the shuttle within the housing.

Housing main body 24 is further shown in FIGS. 5a-5d and is made of transparent plastic. Internal key or rib 89 extends longitudinally for guiding the syringe shuttle. A pair of angularly spaced ledges or interior ribs 91 and 94 support a damping collar 340. An axially extending spline 95 serves to rotatably fix collar 340 within the housing. A set of circumferentially spaced retention snaps 97 serve to axially locate a follower 250.

Figure 6A:
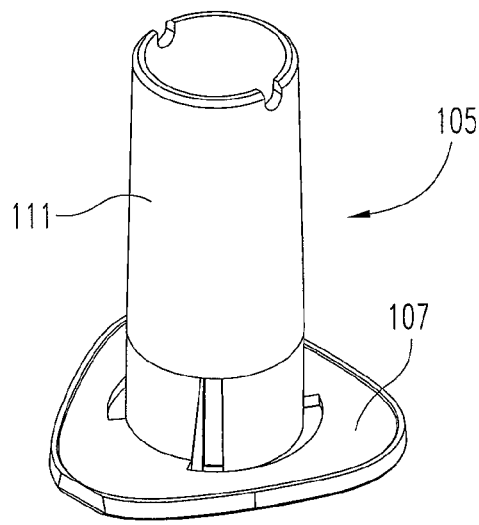
FIGS. 6a, 6b and 6c are respectively perspective, bottom and longitudinal cross-sectional views of a housing baseplate shown separate from the other device components.
Figure 6B:
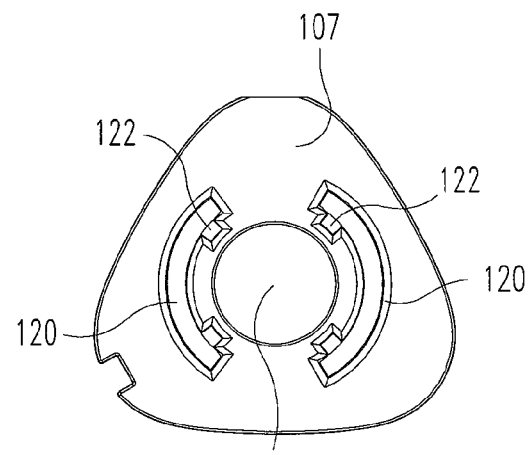
Figure 6C:
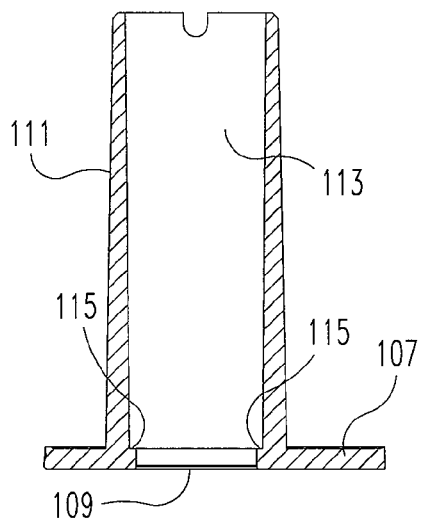
Figure 7A:
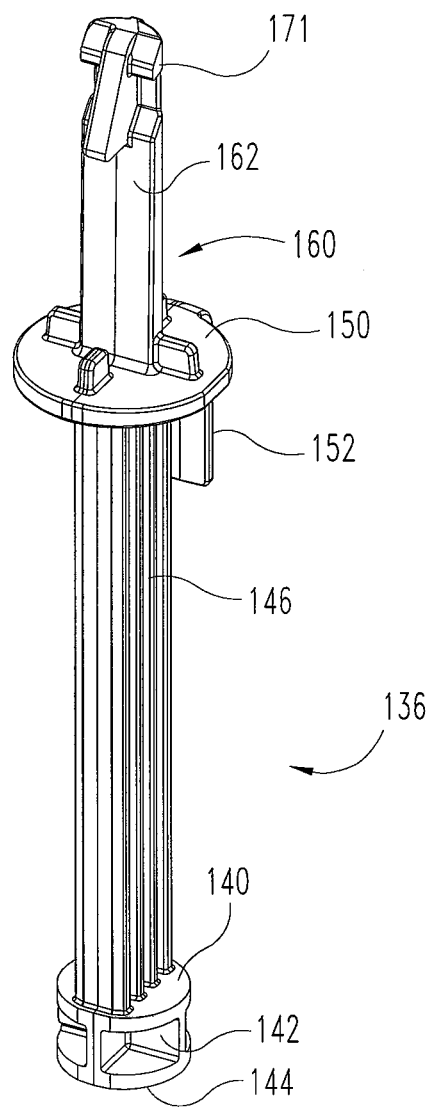
FIGS. 7a, 7b, 7c, 7d and 7e are respectively two perspective, two side, and partial side views of a plunger element shown separate from the other device components.
Figure 7B:
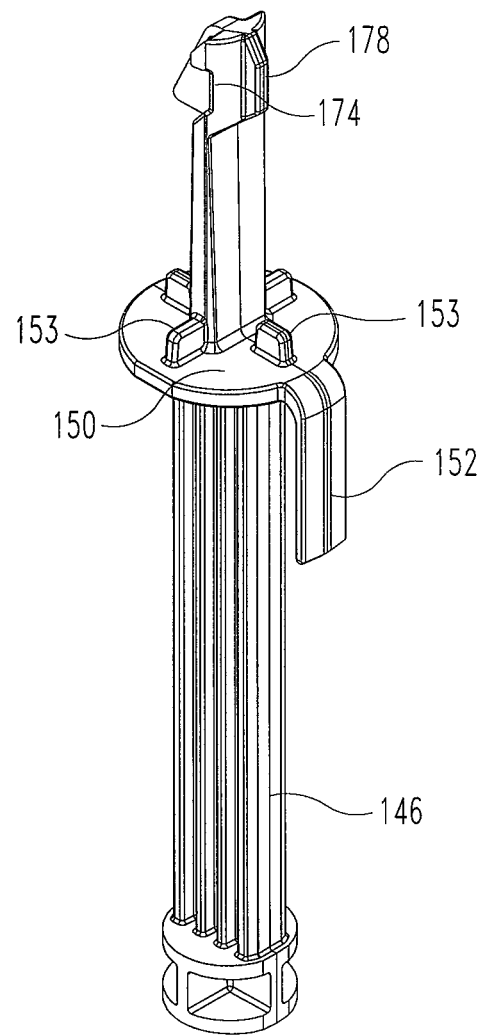
Figure 7C:
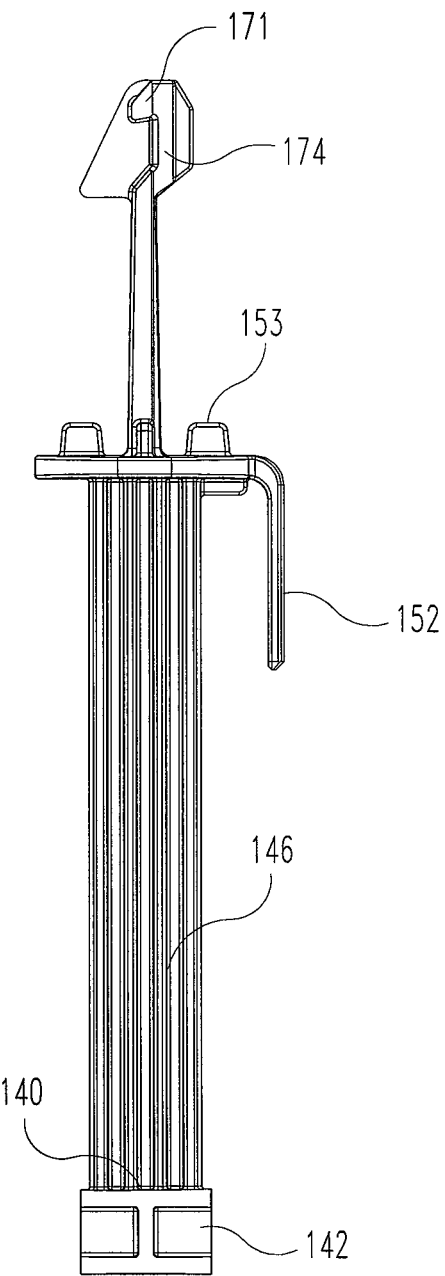
Figure 7D:
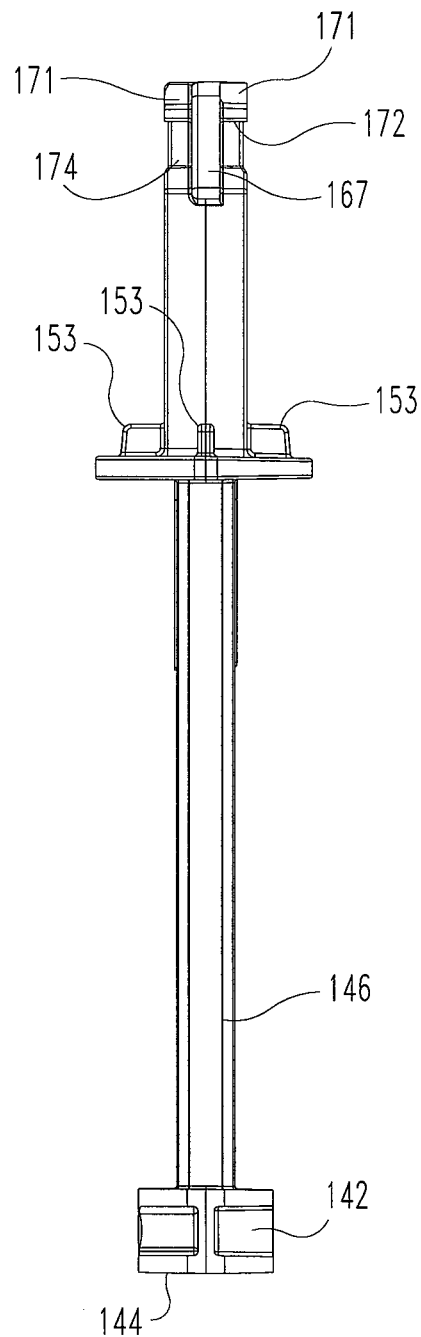
Figure 7E:
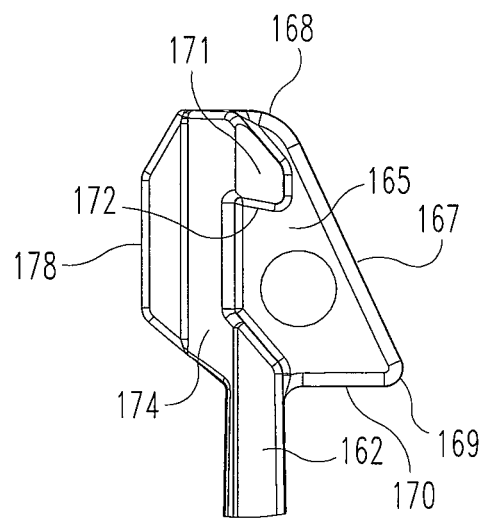

The housing 22 of device 20 includes a baseplate 105 further shown in FIGS. 6a-6c. Baseplate 105 is made of the same material as housing main body 24 and includes a generally trilobular bottom portion 107 keyed to fit within the proximal end of housing main body 24. A central aperture 109 of bottom portion 107 is where a syringe needle moves out from and then back into the housing during use. Tube portion 111 includes a hollow interior 113 in which the syringe is movable. Aperture 109 is sized such that a lip region 115 of bottom portion 107 juts inward relative to tube portion 111 to close off the bottom of a ring-shaped region of interior hollow 113. Lip region 115 prevents the syringe barrel from passing through aperture 109. Baseplate 105 is shown including arcuate slots 120 with ramp features 122 that accommodate a not shown overcap with detented ears that when removed from the housing removes a sterility barrier over the needle prior to device use.

Device 20 includes a medication-filled syringe that other than its plunger element is of conventional design. As shown in FIG. 2, the syringe, generally designated 130, includes a barrel 132 with a flange 133, and an injection needle 134 mounted at the proximal end of the barrel and in fluid communication with the medication contents of the barrel. Although needle 134 is shown as a single needle and is generally expected to be sized for subcutaneous delivery, with adaptions the device could be equipped with a needle of various sizes or types known in the art, including, but not limited to, a needle formed of one or more shortened injection needles, including microneedle arrays, and which needle allows for injection at different depths, such as intradermal.

The plunger mechanism includes a plunger element, generally designated 136, and an elastomeric sealing member or piston 138 that seals the medication within barrel 132.

Plunger element 136 is molded as a single piece of a lightweight but sturdy and sufficiently resilient material, such as Delrin® 311DP from Dupont Engineering Polymers. As further shown in FIGS. 7a, 7b, 7c, 7d and 7e, plunger element 136 includes a cylindrical foot 140 which is hollowed so as to have a cruciform center 142. The proximal face 144 of foot 140 operationally abuts sealing piston 138 during plunger advancement. A ribbed bar 146 rigidly or inflexibly extends axially upward from the top of foot 140 to a disc-shaped flange 150 that has a larger diameter than foot 140. A depending bar 152 is formed on the outer radial periphery of flange 150 and extends axially and proximally from flange 150 in spaced relationship with plunger bar 146.

Four equally angularly spaced bosses 153 upwardly project from flange 150. Bosses 153 aid in centering the drive coil spring 155 shown in FIG. 2 that acts on flange 150 to bias plunger element 136 downward within device 20.

Plunger element 136 includes one and only one resilient prong, generally designated 160, that serves as part of the trigger assembly. The single prong 160 latchably engages a shuttle in the shown embodiment until released by the plunging of button 25, which release allows the spring 155 to bias the plunger element 136 downward to result in needle insertion and injection.

Prong 160 includes an upstanding, tapering finger 162 that projects axially from the center of flange 150 so as to be centered on the axis of the housing 22. Finger 162 is flexible due to its construction to allow its bending movement when the prong is acted on for its release. Prong 160 includes a triangular projection 165 centered on the side to side width of finger 162. Projection 165 includes a ramp surface 167 extending distally and at an angle inward from the tip 169 of the projection 165 to form an outward facing ramp used in camming of the prong for release. Ramp surface 167 extends from tip 169 to a distal end 168. The lower face 170 of projection 165, which face does not serve a latching function, is transverse to the axial direction.

A pair of latching surfaces 172 is provided on the uppermost portions 171 of extensions 174 of finger 162. Latching surfaces 172 and extensions 174 flank either side of projection 165 and are spaced radially inward from the ramp surface 167 at the height of the latching surfaces along prong 160. Latching surfaces 172 are provided generally in axial alignment with finger 162 and each is formed with a slight undercut so as to slope slightly proximally as it extends in the radial direction toward ramp surface 167. Latching surfaces 172 are disposed at a height between the axial extent of ramp surface 167, such as near the distal end 168. In this location, the contacting forces on the ramp surface will tend to produce a translational deflection of the latching element which may have a lower and more consistent unlatching force than would a rocking or pivoting motion, caused by the latching surfaces being substantially above or below the ramp surface, that would introduce extra deformation of prong 160 and make the unlatching motion less smooth.

The back surface of projection 165 juts rearward beyond extensions 174 to define a safety protuberance 178. Protuberance is backed up by safety arm 72 when button 25 is in its locked orientation.

Figure 8A:
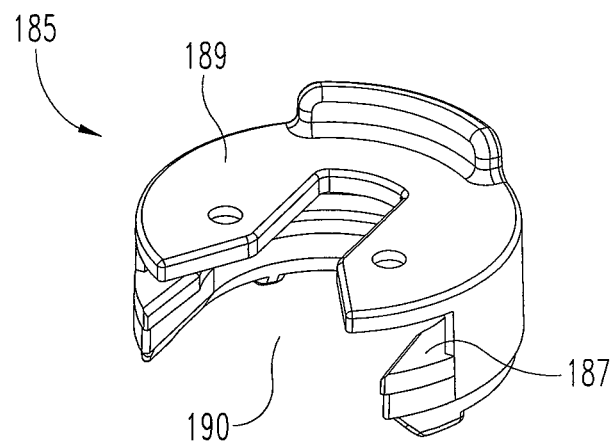
FIGS. 8a and 8b are respectively top and bottom perspective views of a syringe carriage shown separate from the other device components.
Figure 8B:
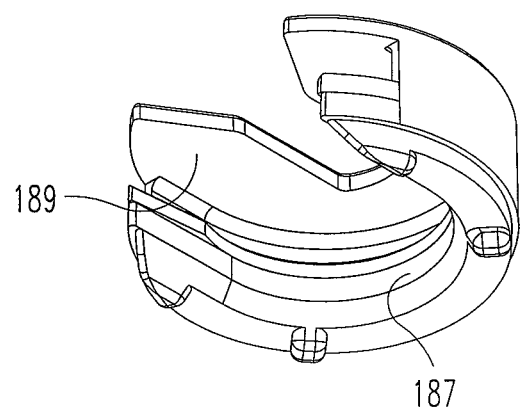
Figure 9A:
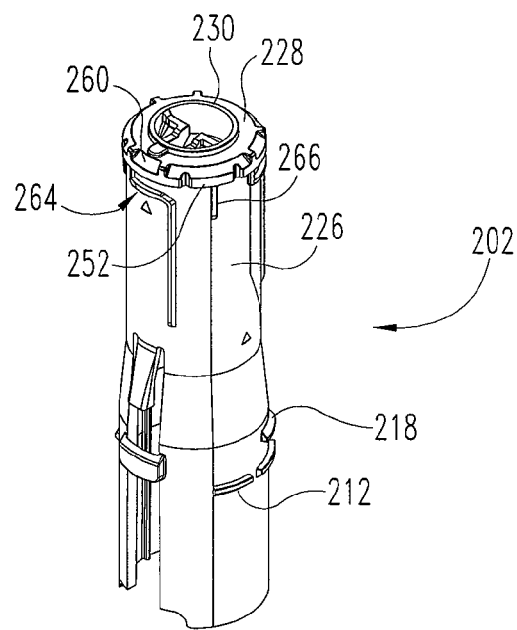
FIGS. 9a, 9b, 9c, 9d, 9e, 9f, and 9g are respectively perspective, first side, second side, top, longitudinal cross-sectional, bottom, and third side views of an upper shuttle part shown separate from the other device components.
Figure 9B:
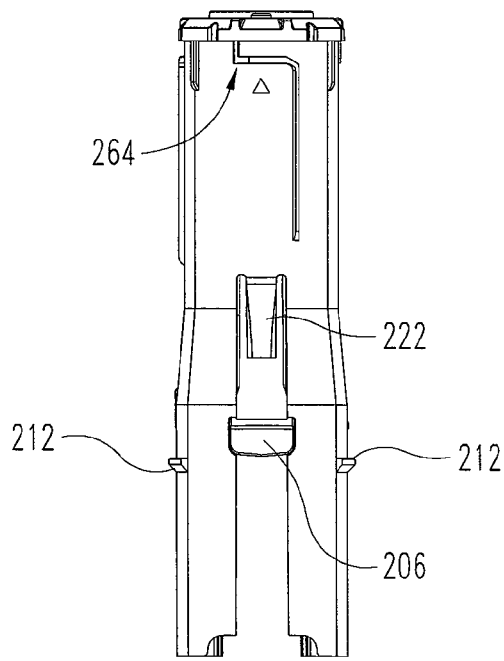
Figure 9C:
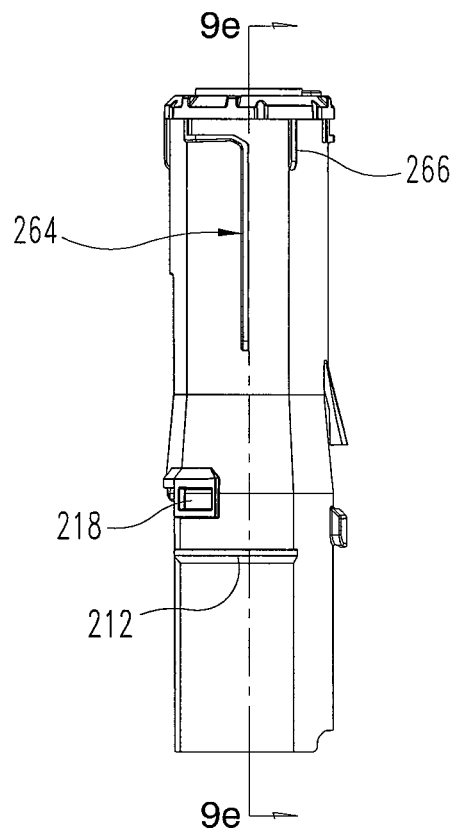
Figure 9D:
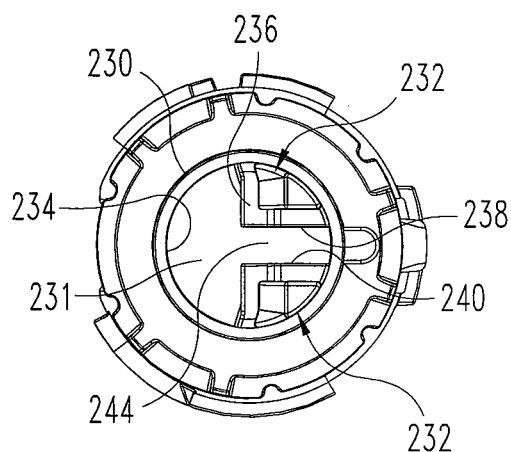
Figure 9E:
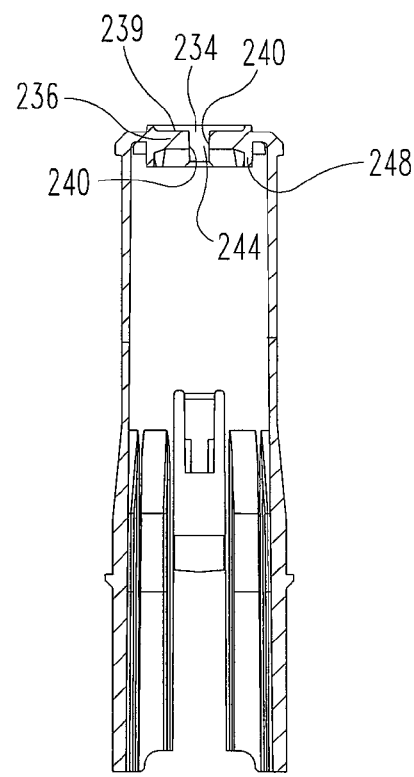
Figure 9F:
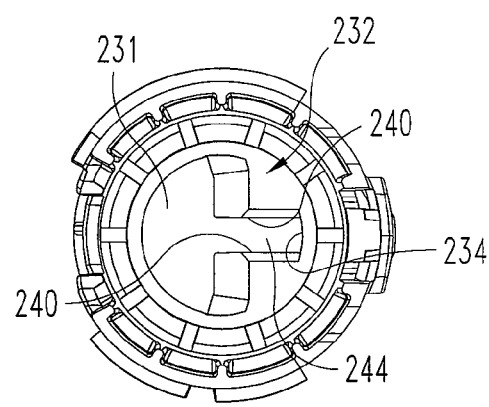
Figure 9G:
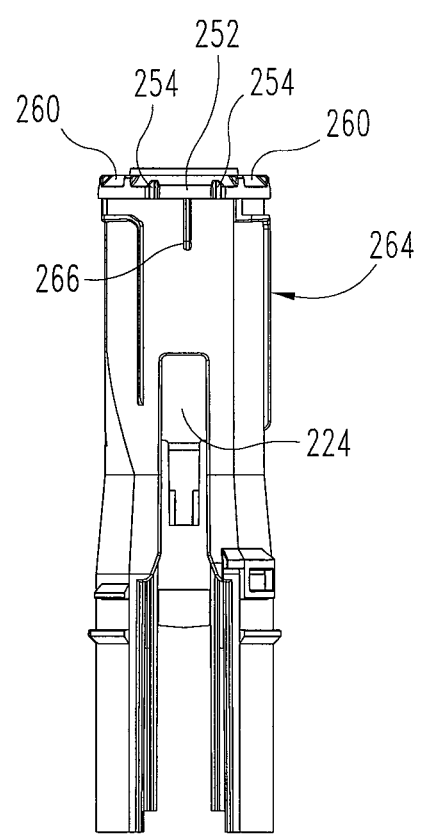
Figure 10A:
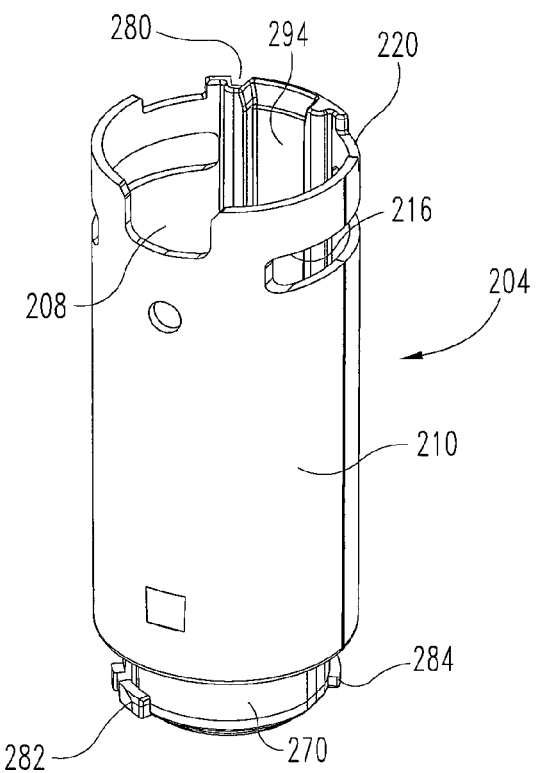
FIGS. 10a, 10b, 10c, 10d and 10e are respectively perspective, first side, longitudinal cross-sectional, top and bottom views of a lower shuttle part shown separate from the other device components.
Figure 10B:
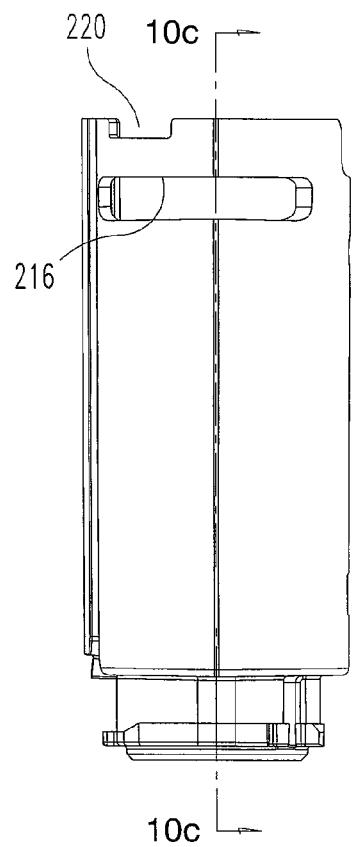
Figure 10C:
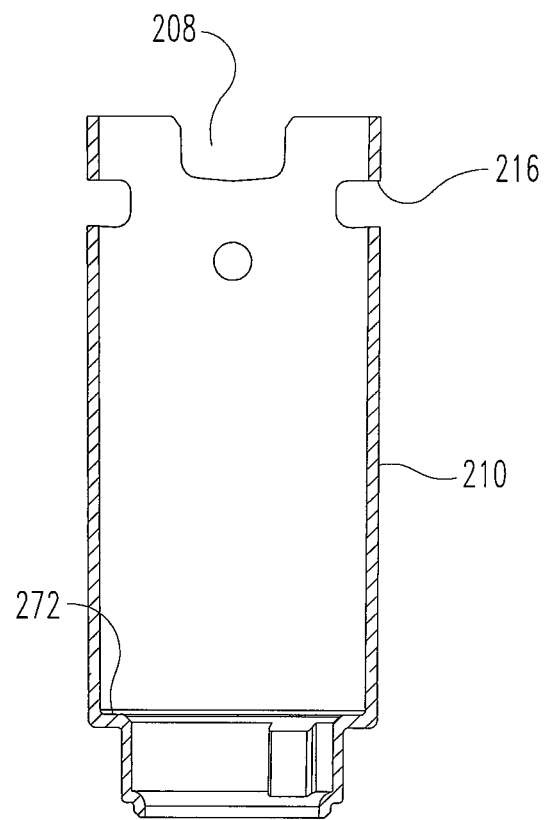
Figure 10D:
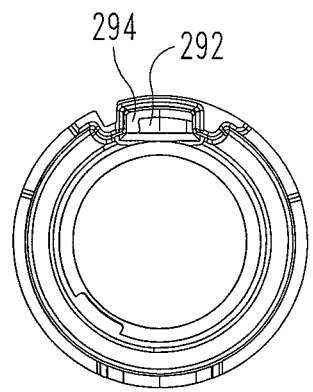
Figure 10E:
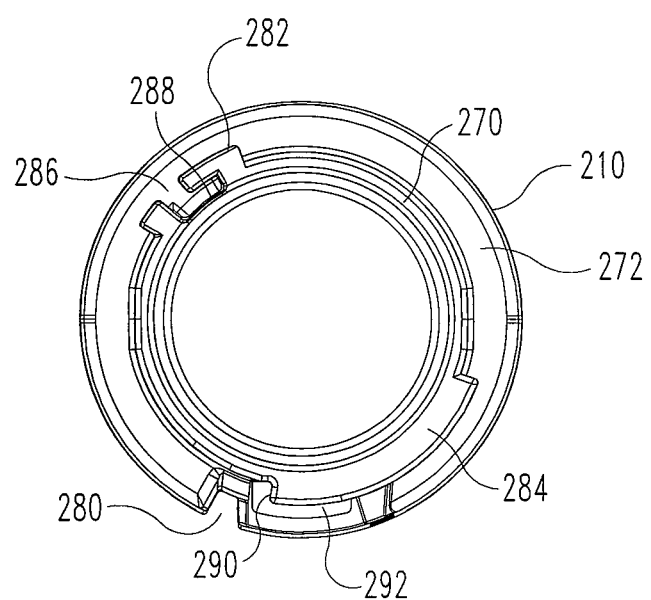
Figure 11A:
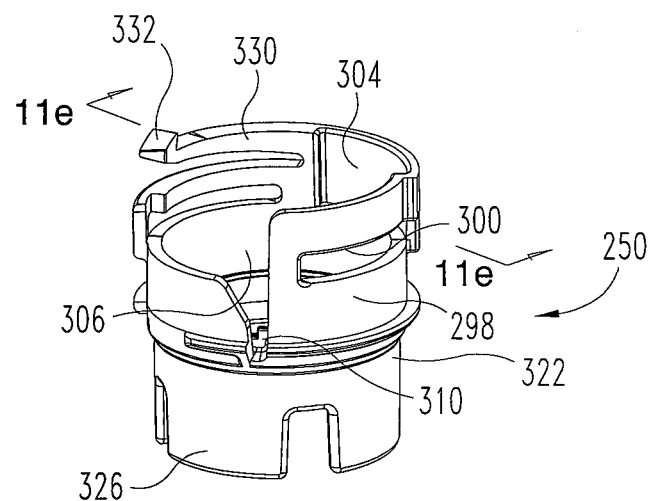
FIGS. 11a, 11b, 11c, 11d and 11e are respectively first perspective, first side, second perspective, second side and longitudinal cross-sectional views of a follower shown separate from the other device components.
Figure 11B:
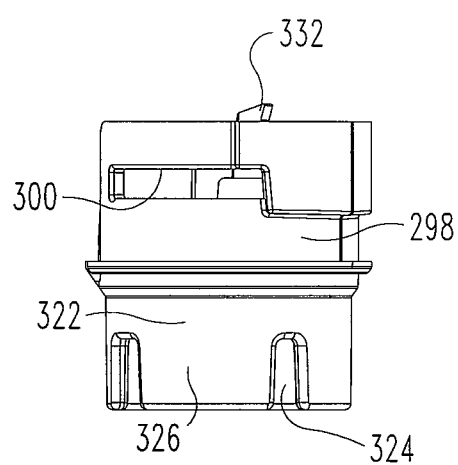
Figure 11C:
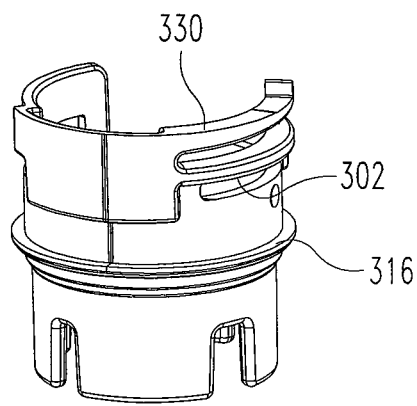
Figure 11D:
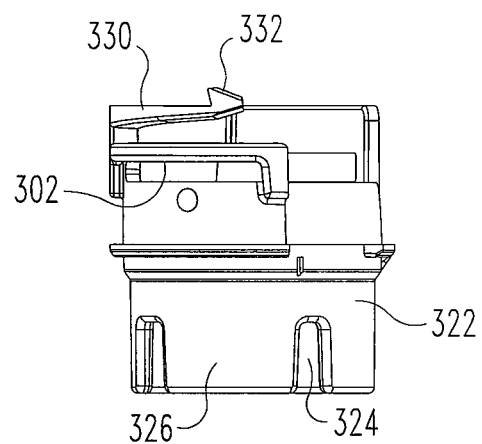
Figure 11E:
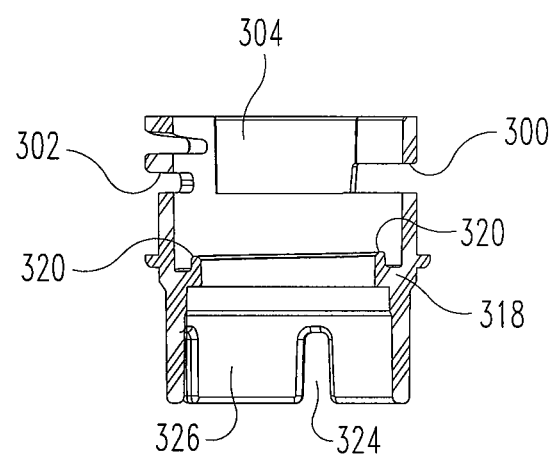
Figure 12A:
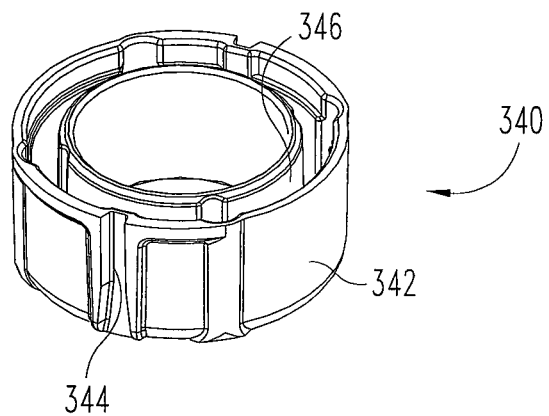
FIGS. 12a, 12b, 12c and 12d are respectively perspective, side, longitudinal cross-sectional and top views of a grease collar shown separate from the other device components.
Figure 12B:
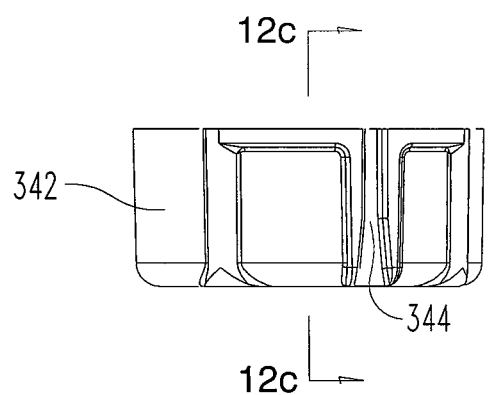
Figure 12C:
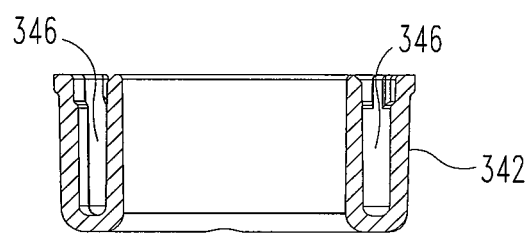
Figure 12D:
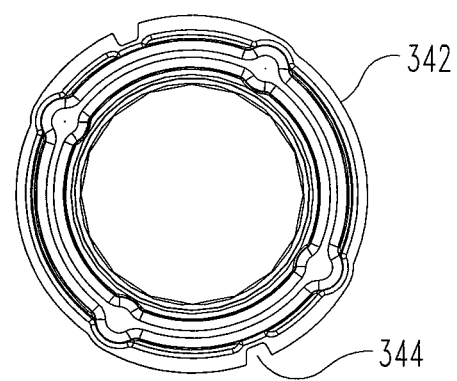
Figure 13:
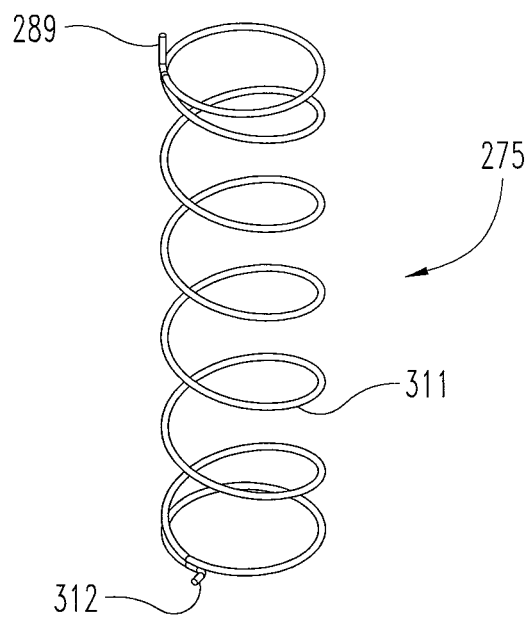
FIG. 13 is a perspective view of a spring shown separate from the other device components.

An overmolded syringe carriage 185 for device 20 is further shown in FIGS. 8a and 8b and fits over syringe barrel flange 133. Syringe carriage 185 includes a rigid base formed of a C-shaped lower region 187 and an apertured top region 189. The carriage base defines a cavity 190 into which syringe flange 133 can be inserted from the side during device assembly such that carriage 185 captures the flange axially. A softer overmolding of lower region 187 provides a cushioning to reduce the likelihood of breakage of the glass syringe during use, and to soften the sound made by an actuating device. The underside of aperture top region 189 faces for direct supportive engagement the upper surface of foot 140.

Device 20 has a delay mechanism that includes a shuttle, generally designated 200, a follower 250 that releasably latches with the shuttle 200, and a dual functioning biasing member 275 acting between the shuttle and the follower. Shuttle 200 is formed of an upper shuttle 202 and a lower shuttle 204 further shown in FIGS. 9a-9g and FIGS. 10a-10e, respectively, that are fixedly connected during manufacturing assembly.

A protruding alignment key 206 of upper shuttle 202 closely fits within a notch 208 formed in body 210 of lower shuttle 204. Lips 212 provided on opposite sides of upper shuttle 202 snap lock over ledges 216 of lower shuttle 204. Keys 218 projecting from the periphery of upper shuttle 202 fit into notches 220 formed in lower shuttle body 210. The fitting of keys 218 within notches 220 and key 206 within notch 208 rotatably fixes the shuttle parts together when connected.

A locking flexure 222 outwardly extends at an angle from upper shuttle 202 and cooperates with the lock ledge 92 of sleeve 26 to secure the shuttle in a retracted position after use. Slot 224 accommodates plunger bar 152.

The upper portion of upper shuttle 202 is a tubular, cylindrical body 226 with a cap portion 228 that rings an annular collar section 230. An opening 231 defined by collar section 230 is circular other than as interrupted by a pair of mirror-image projections 232 that jut inward from the axially extending interior surface 234 of collar section 230. Each projection 232 includes a latch region 236 and a guide region 238 that are orthogonally arranged. The top surface 239 of latch region 236 serves as a latch surface of the trigger assembly. Latch surface 239 is ramped upward to be complementary to the undercut of latching surfaces 172 to provide a more secure but releasable connection therebetween.

The facing surfaces 240 of the two projections 232 are in spaced apart relationship to define along with collar surface 234 a U-shaped section 244 of opening 231 in which the button flange portion 52 closely fits when inserted therein during button plunging. Collar surface 234 within opening section 244 serves as a support surface that hinders outward radial motion of flange portion 52 by abutting engagement with button surface 56 during button plunging. Facing surfaces 240 serve as support surfaces that hinder twisting motion of flange portion 52 by abutting engagement with the side surfaces of flange portion 52, including ribs 67, during button plunging. Collar surface 234 and the two facing surfaces 240, due to their size and shaping complementary to the transverse cross-sectional shape of flange portion 52, provide a transverse containment of the flange portion 52 which limits flange twisting and button tilting within the housing.

The underside 248 of collar section 230 centers the distal end of spring 155. The outer rim of cap portion 228 includes three circumferentially spaced land sections 252 having ends defined by indents 254. Land sections 252 and indents 254 cooperate with button fingers 42 and detents 44 to aid in keeping the button in one of two preferred rotational positions relative to the shuttle 200. Three beveled sections 260 alternating with land sections 252 are provided over which snap fit button fingers 46 with stops 48.

A series of multi-angled stop ribs, generally designated 264, and axially extending stop ribs 266 cooperate with button stops 48 to encourage proper device operation by frustrating manual button plunging when the button is not in an unlocked state, by preventing button 25 from being rotated in the wrong direction from a locked state or being rotated too far during unlocking, by guiding the downward travel of the button during its plunging, and by preventing manual relocking of the sleeve 26 during fluid delivery.

Lower shuttle 204 includes proximal region 270, and the flange 272 that transitions from body 210 to region 270 is designed to engage syringe carriage 185. Groove 280 in lower shuttle body 210 receives housing key 89 to rotatably fix shuttle 200 with housing 22.

Tabs 282 and 284 radially project from proximal region 270 and serve as latching elements or hooks to engage the follower. Notch 286 that leads to pocket 288 within tab 282 receives an upper projection 289 of the biasing member 275.

An angled, locking latch surface 290 is disposed proximally of an opening 292 in line with an axially extending channel 294 formed in the interior surface of lower shuttle body 210. Channel 294 accommodates plunger arm 152 that can project through opening 292 to unlock the locking mechanism described below.

Follower 250 is further shown in FIGS. 11a-11e and includes an upper portion 298 with ledges 300 and 302 that serve as latching elements that engage shuttle latching tabs 282 and 284. Channel 304 and opening 306 in upper portion 298 allow axial movement of tabs 282 and 284 therein for manufacturing assembly and for shuttle release relative to the follower during device use. Opening 306 tapers to a slot-shaped portion 310 adapted to closely receive a radial projection 312 of biasing member 275.

A radially projecting flange 316 snaps past housing snaps 97 during device assembly. The interior surface of follower portion 298 includes an inwardly projecting ring 318 with a spring centering lip 320.

A sleeve shaped lower portion 322 of follower 250 depends from follower portion 298 and has a lesser diameter. Slots 324 in the proximal edge of portion 322 define four damping fins 326 of the follower.

A locking member for follower 250 to limit its rotation relative to the shuttle 200 is formed as a flexure arm 330 with an upwardly extending latch 332 at its end.

Biasing member 275 functions as both a torsion spring and a compression spring, with its torsional force and axial force resulting from a release of a torsional preloading and an axial preloading accomplished during the manufacturing assembly of device 20. Biasing member 275 is shown as a cylindrical spring formed of a helically coiled wire 311, with a shuttle engaging tip 289 and a follow engaging tip 312.

Grease collar 340, further shown in FIGS. 12a-12d, provides a support surface for the damping fluid as the follower 250 rotates relative to that support surface. Collar 340 includes an annular body 342 through which fits the syringe barrel. Collar 340 is axially supported within housing 22 by ledges 91 and keyed to the housing via a rib defined slot 344 that fits over housing spline 95. Collar body 342 includes a generally U-shaped wall that defines an annular hollow 346.

A damping compound 350, such as a silicone grease thickened with Teflon, fills annular hollow 346. Follower fins 326 fit within hollow 346 such that compound 350 is disposed both radially inward and outward of such fins 326, as well as between adjacent fins 326 and as a film between the fin undersides and the base of the collar wall, resulting in a damping or delay effect as the follower fins 326 try to rotate relative to the collar.

Figure 14:
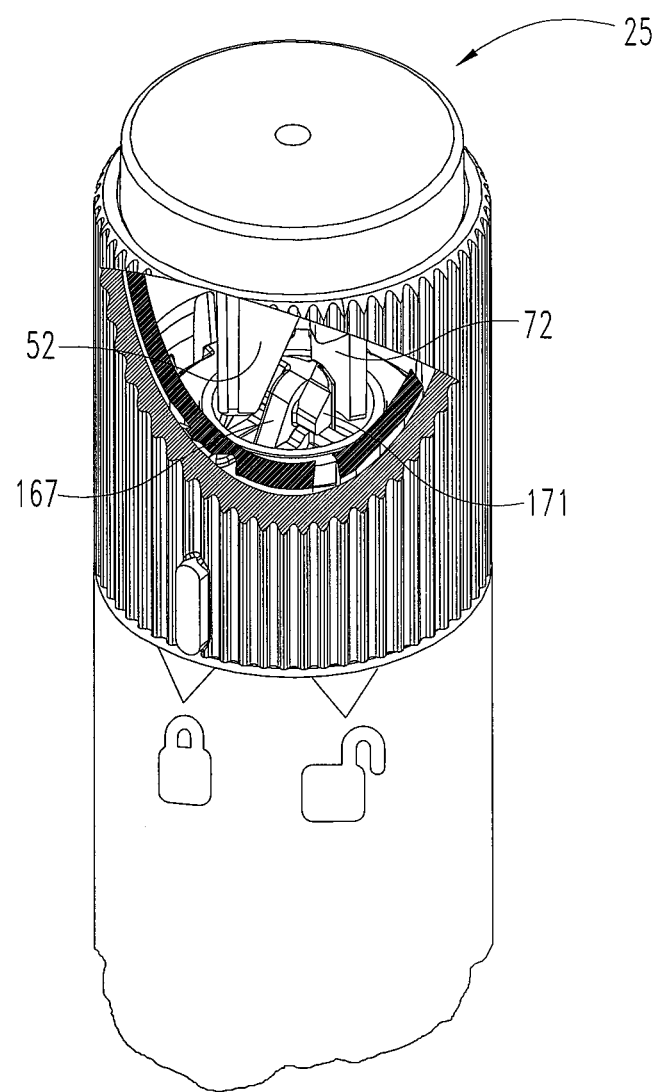
FIG. 14 is a partial perspective view of the automatic injection device of FIG. 1 in a locked arrangement, wherein a portion of the device is cut away further revealing the arrangement of the trigger assembly.

The construction of device 20 will be further understood in view of a description of its operation after the end cap is removed in preparation for an injection. The device 20 is configured in a locked state as shown in FIGS. 2 and 14. If a user applies a plunging force on button 25, button travel is frustrated by button stops 48 axially abutting shuttle ribs 264. Triggering is also frustrated by tapered flange portion 52 not being aligned to operationally engage ramp surface 167. Safety arm 72 is disposed within opening 231 in a position backing up prong protuberance 178, and safety arm is prevented from moving outward by collar interior surface 234, to prevent prong 160 from unlatching from the shuttle.

Figure 15:
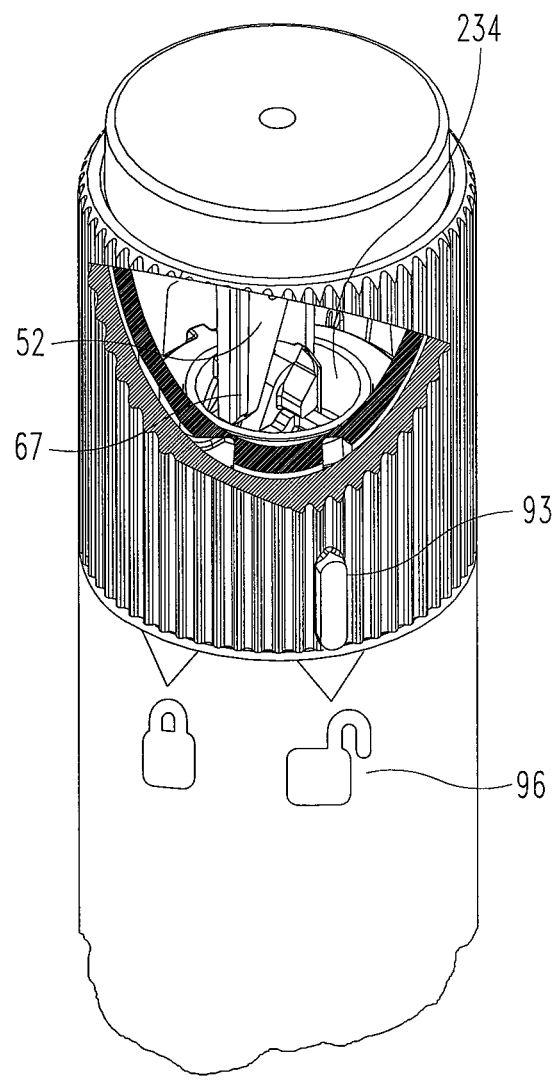
FIG. 15 is a partial perspective and cutaway view similar to FIG. 14 after the automatic injection device has been unlocked by manual rotation of the safety sleeve, and thereby the button, into a ready to operate arrangement.
Figure 16:
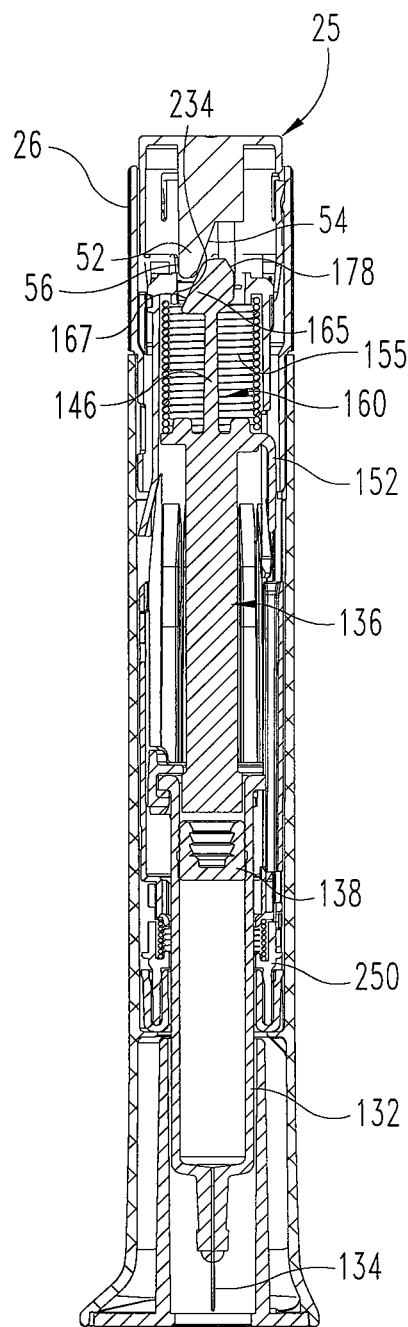
FIG. 16 is a longitudinal cross-sectional view of the automatic injection device of FIG. 15 in its ready to operate arrangement.

To arrange device 20 to inject, locking sleeve 26, and thereby button 25, is manually rotated by a user to a prepared or ready to inject state at which indicator 93 on sleeve 26 aligns with unlock icon 96. When so prepared, device 20 is arranged as shown in FIGS. 15 and 16. In this arrangement, tapered flange portion 52 is operationally aligned in the same plane with triangular projection 165, and with flange surface 54 directly facing ramp surface 167 and with flange surface 56 adjacent and directly facing the collar interior surface 234. Safety arm 72 is still disposed within opening 231 but is now out of radial alignment with protuberance 178 so as to not prevent prong 160 from moving so as to unlatch from the shuttle.

Figure 17:
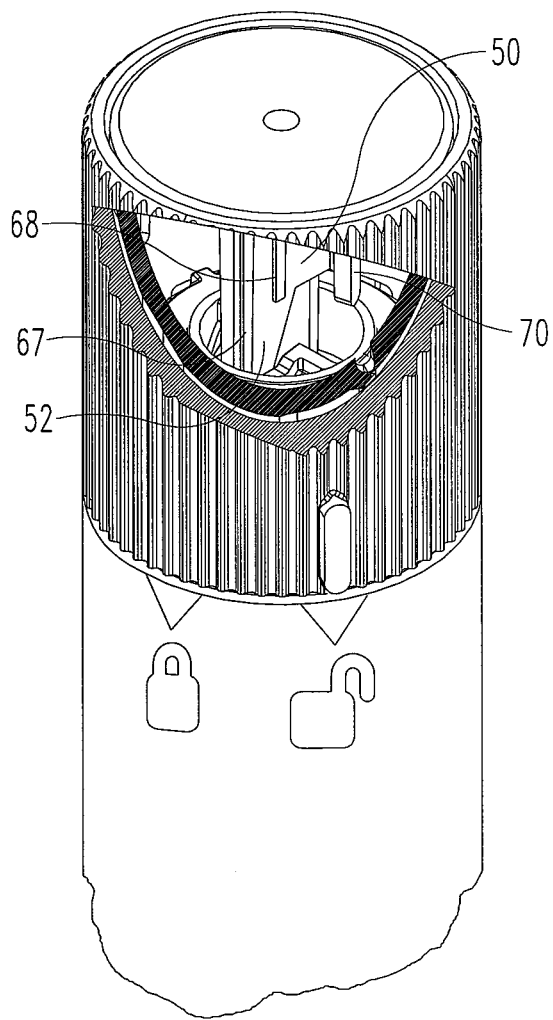
FIG. 17 is a partial perspective and cutaway view similar to FIG. 14 after the automatic injection device has been triggered for injection.
Figure 18:
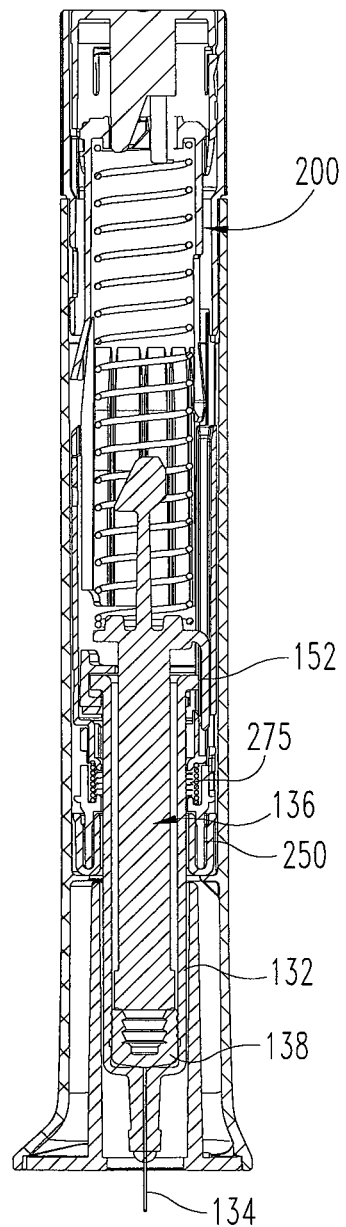
FIG. 18 is a longitudinal cross-sectional view of the automatic injection device of FIG. 17.

When a user subsequently applies a plunging force on button 25, button 25 starts to move downward into sleeve 26, thereby driving flange surface 54 against ramp surface 167. As button 25 continues to move further downward, with flange portion 52 inserting further into shuttle opening 231, flange surface 54 slides along ramp surface 167. During this sliding, flange portion 52 cams prong 160 radially outward because flange portion 52 is prevented from bending in the opposite radially outward direction due to the contact with the supportive collar surface 234. Flange portion 52 is prevented from twisting due to the contact with the supportive surfaces 240. Prong 160 can be cammed outward as finger 162 bends until latching surfaces 172 disengage from latch surfaces 239, at which point the uppermost portion of plunger prong 160 passes downward through the shuttle opening 231 due to spring 155 directly biasing the plunger element 136 downward to drive it and thereby the syringe piston 138 proximally, which driven motion shifts syringe barrel 132 proximally relative to the shuttle and the housing to cause the tip of needle 134 to project beyond the housing proximal end for penetrating a user's skin, and then forces the medication contents of the syringe through that needle for an injection As plunger element 136 moves proximally during medication injection, the bar 152 causes a disengagement of latch 332 to unlock the follower 250 for rotation. FIGS. 17 and 18 show the arrangement of device 20 at this point of the use process.

Follower 250, as urged by the torsional preloading of biasing member 275, rotates against the damping effect of damping compound 350, during which rotation remaining medication can be properly expelled from the syringe through the needle. When follower 250 has rotated such that shuttle tabs 282 and 284 are clear of ledges 300 and 302, shuttle 200 and follower 250 are thereby unlatched so as to allow the compressive preloading of biasing member 275 to force shuttle 200 upward to retract the proximal tip of the injection needle 134 to a protected position within the housing 24.

Figure 19:
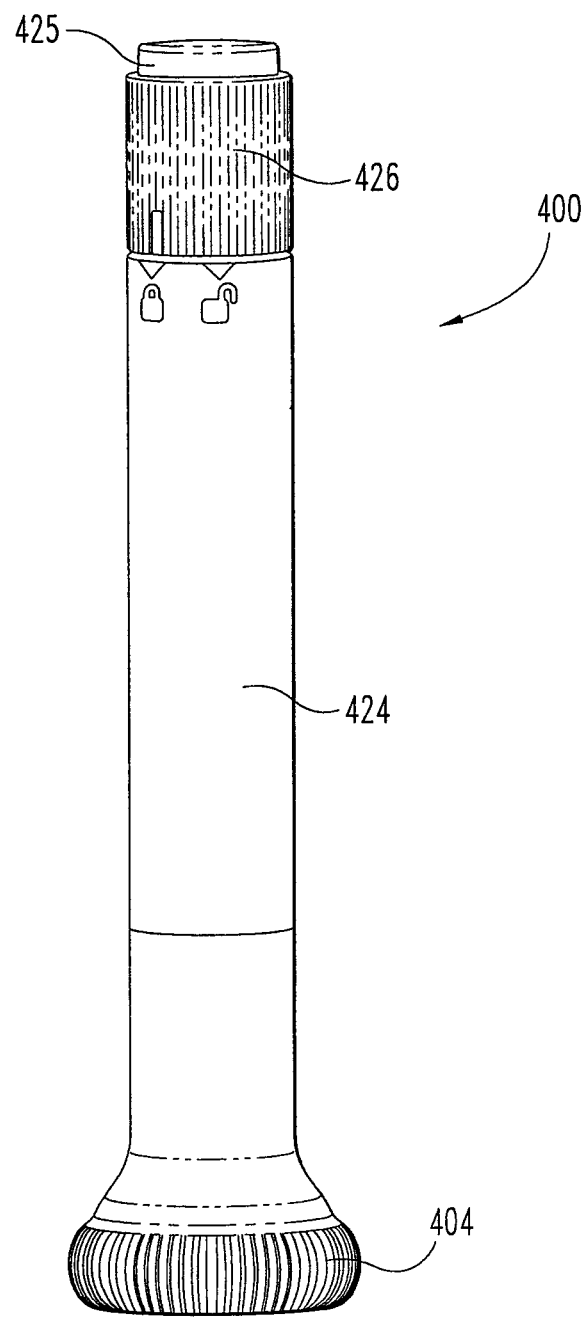
FIG. 19 is a side view of another automatic injection device with a trigger assembly of the present invention.

Referring now to FIG. 19, there is shown another automatic injection device, generally designated 400, with a trigger assembly of the present invention. Device 400 is substantially similar to device 20 with respect to its overall operation, and from the standpoint of the user it appears to work identically other than the manner in which the overcap 404 may be twisted off or be pulled off rather than only being able to be pulled off. Device 400 includes main body 424, rotatable safety sleeve 426 and button 425. Differences in device 400 from device 20 visible to a user include that device 400 is slighter taller overall, due to it having a taller syringe filled with a larger volume of medication, as well as its larger, knurled overcap 404.

Device 400 includes a drive coil spring, a dual functioning spring acting between a follower and a shuttle, a damping collar and a syringe carriage that are identical to those of device 20, and thus are not separately shown herein. The syringe portions of device 400 other than the plunger element are not shown, but may be similar to that shown in device 20, with the syringe being taller overall to hold more medication.

Device 400 further includes a variety of component parts that differ slightly from the corresponding parts of device 20, primarily due to the taller height of the device, and these parts are shown in FIGS. 20-27. As these parts are essentially the same as their corresponding parts of device 20, only certain differences from such parts are noted.

Figure 20:
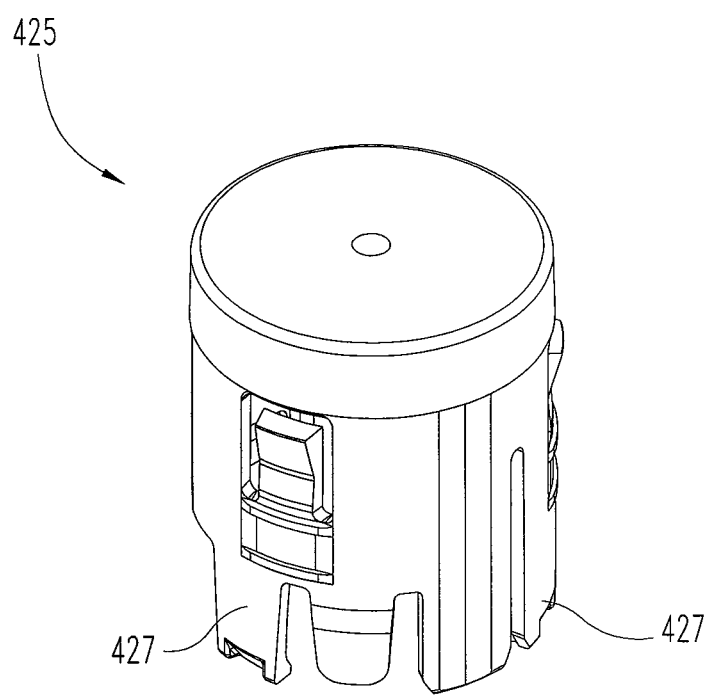
FIG. 20 is a perspective view of a button shown separate from the other components of the device of FIG. 19.

Button 425 shown in FIG. 20 includes three fingers 427 that are thickened on their radially inside regions to provide for a more robust attachment to the shuttle.

Figure 21A:
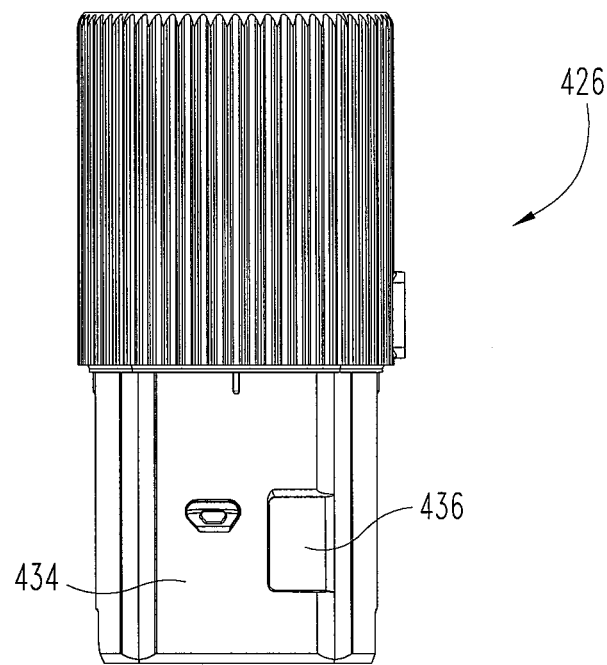
FIGS. 21a and 21b are respectively side and bottom views of a housing sleeve shown separate from the other components of the device of FIG. 19.
Figure 21B:
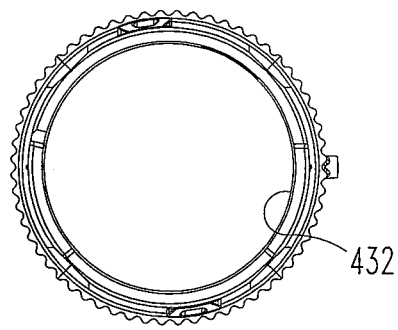
Figure 22A:
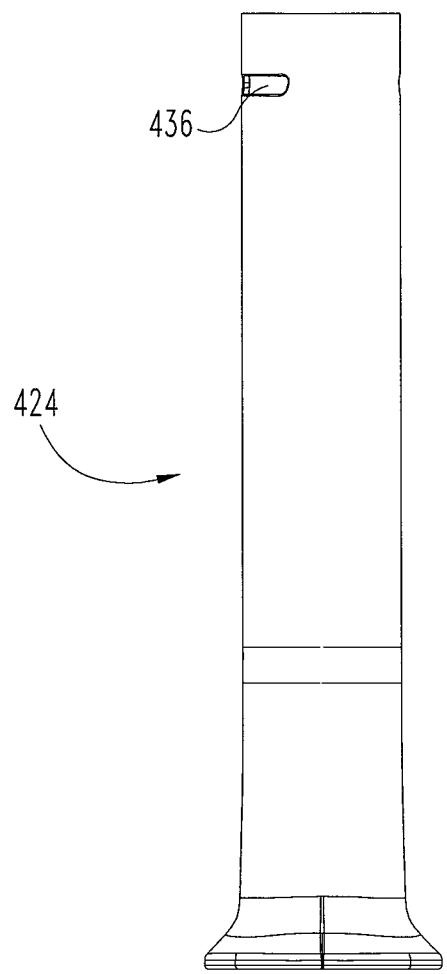
FIGS. 22a, 22b, 22c and 22d are respectively side, first longitudinal cross-sectional, second longitudinal cross-sectional and top views of a housing main body shown separate from the other components of the device of FIG. 19.
Figure 22B:
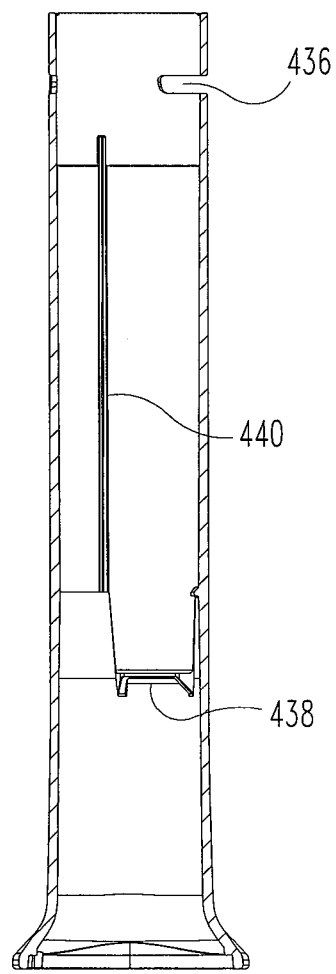
Figure 22C:
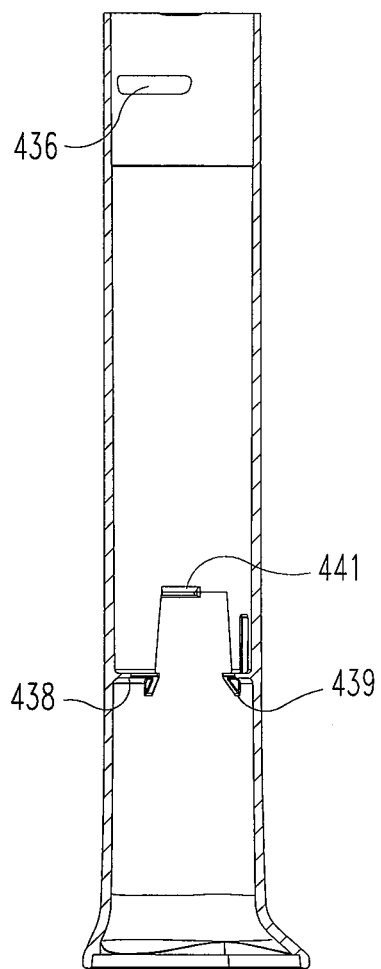
Figure 22D:
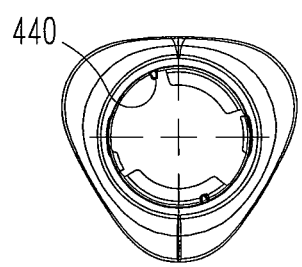

Housing sleeve 426 shown in FIGS. 21a and 21b has a reduced diameter interior 432 to better center the device shuttle therein. Sleeve portion 434 is lengthened proximally, and opening 436 is moved proximally the same amount.

Housing main body 424 shown in FIGS. 22a, 22b, 22c and 22d is lengthened distally. Slots 436 are moved distally the same amount, and rib 440 is lengthened distally the same amount. Collar supporting ledges 438 and 439, and retaining snaps 441, are moved proximally.

Figure 23A:
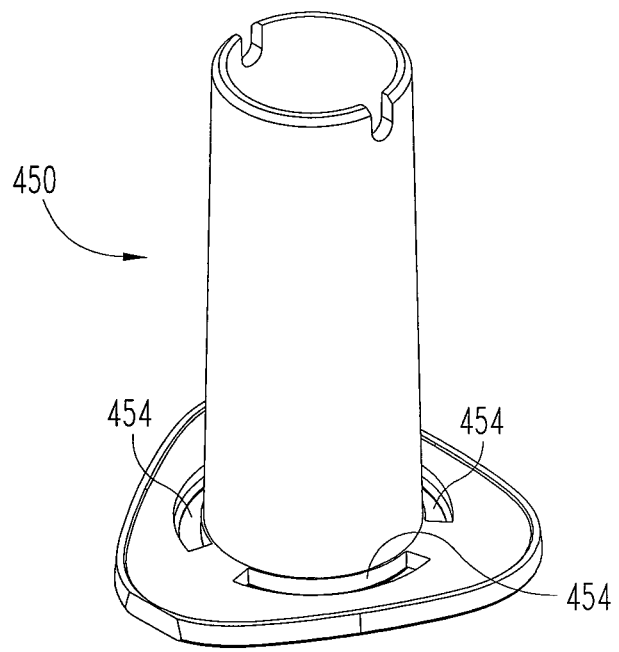
FIGS. 23a, 23b and 23c are respectively perspective, bottom and longitudinal cross-sectional views of a housing baseplate shown separate from the other components of the device of FIG. 19.
Figure 23B:
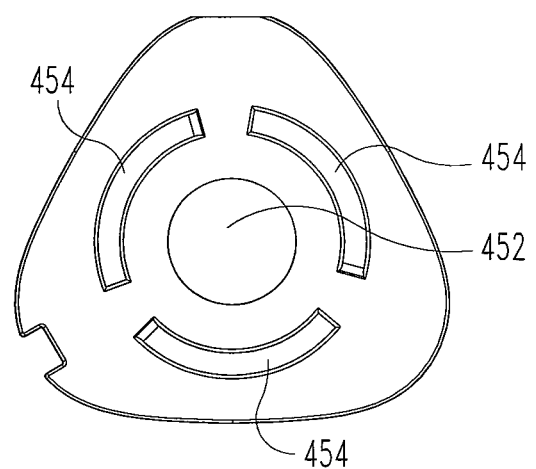
Figure 23C:
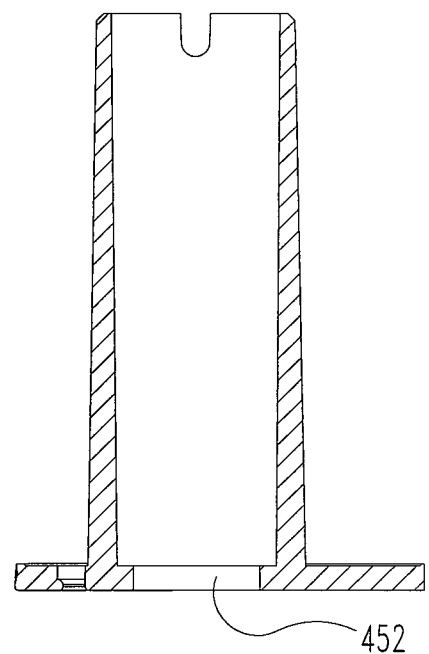
Figure 24A:
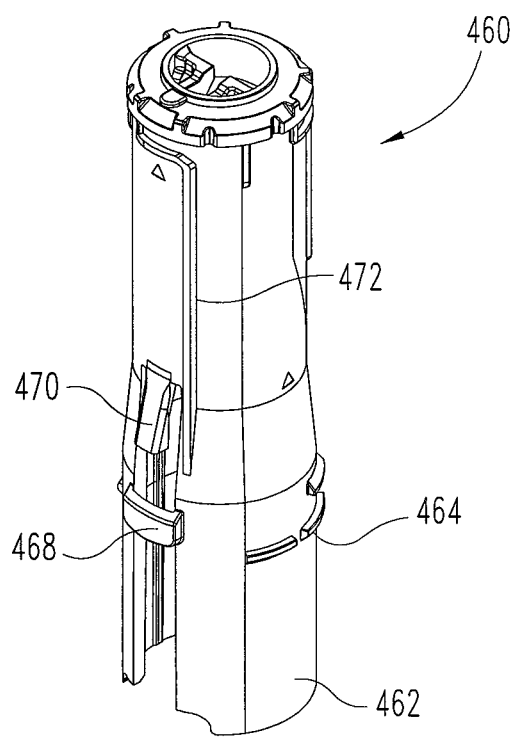
FIGS. 24a, 24b, 24c and 24d are respectively perspective, first side, second side and top views of an upper shuttle part shown separate from the other components of the device of FIG. 19.
Figure 24B:
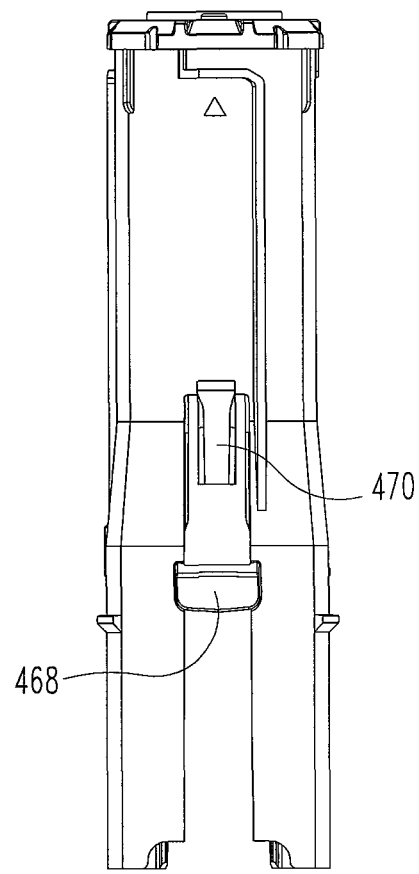
Figure 24C:
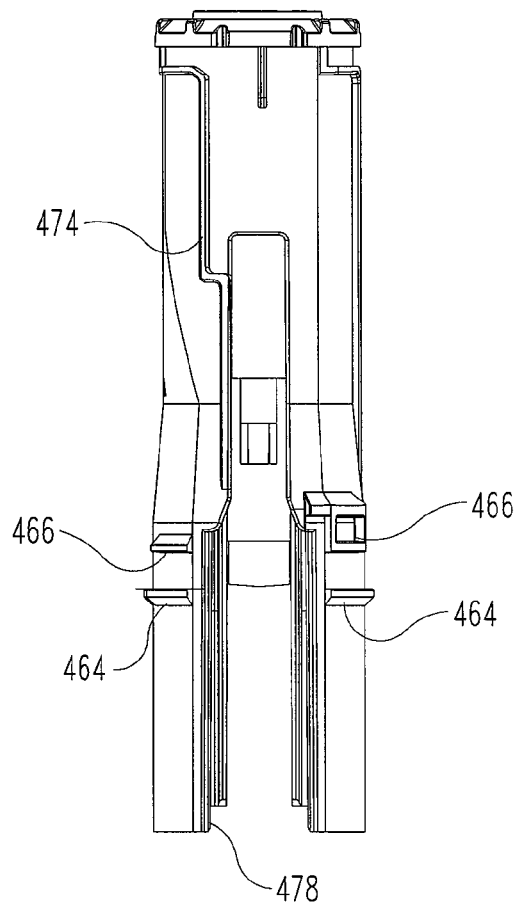
Figure 24D:
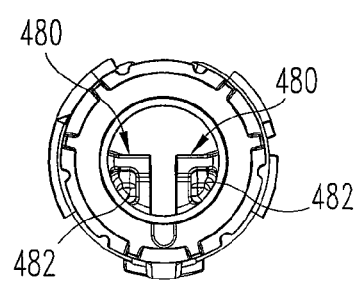

Housing baseplate 450 shown in FIGS. 23a, 23b and 23c is taller overall but has a smaller aperture 452. Baseplate 450 includes three slots 454 that accommodate three not shown, unidirectional camming ears of knurled overcap 404. The overcap cams and baseplate slots cooperate to shift overcap 404 away from baseplate 450 when the overcap is manually twisted in a clockwise fashion relative to the baseplate, which twisting may be done by a user to help with removal of the overcap and the sterility barrier of the syringe needle.

Upper shuttle 460 shown in FIGS. 24a, 24b, 24c and 24d is lengthened to provide a taller shuttle that accommodates a longer plunger element to allow for a larger dose. Shuttle 460 is so lengthened by being extended proximally at 462, and the lips 464, keys 466 and key 468 are similarly moved proximally to allow for secure connection to the lower shuttle. Locking flexure 470 is also moved proximally, and material is added around the base of the flexure to effectively shorten the flexure for a more rigid construction. Along the outer periphery of the shuttle, multi-angled stop ribs 472 and 474 are lengthened proximally and thickened to better center the shuttle within the housing. Stop rib 474 is also provided with a bend.

The stiffening ribs 478 in the interior of the proximal region of upper shuttle 460 are provided with chamfered proximal ends to reduce unintended catching of a spring during device assembly. At its upper end shown in FIG. 24d, upper shuttle 460 is provided with mirror-image projections 480 each having a pocket 482 sized and shaped to define thicker walls that are suitably constant in wall thickness for molding purposes.

Figure 25A:
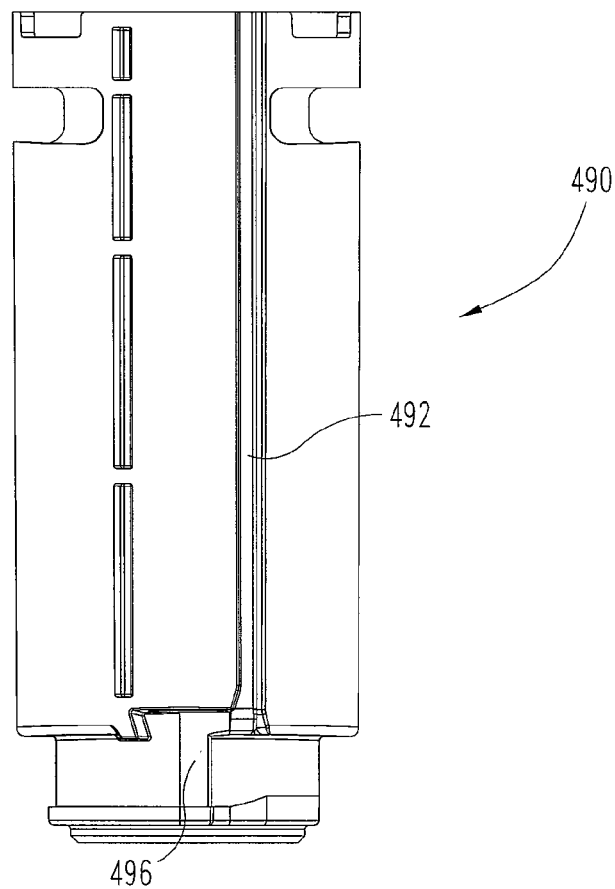
FIGS. 25a and 25b are respectively side and top views of a lower shuttle part shown separate from the other components of the device of FIG. 19.
Figure 25B:
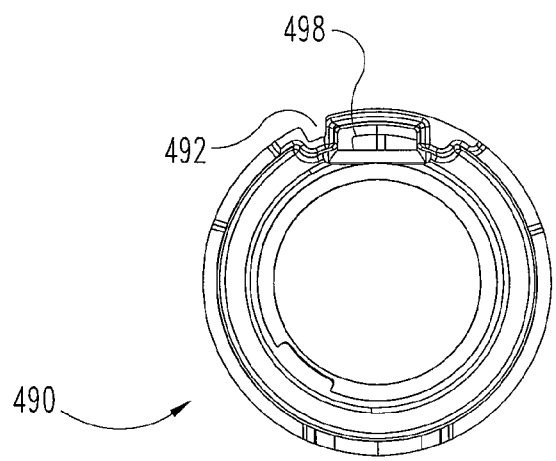

Lower shuttle 490 shown in FIGS. 25a and 25b includes a channel feature 492 having a reduced radial depth, and the complementary rib 440 is correspondingly shaped. The surface 496 disposed proximally of opening 498 extends further radially outward to decrease the radial space into which can extend the plunger bar 522 when projecting through opening 498.

Figure 26:
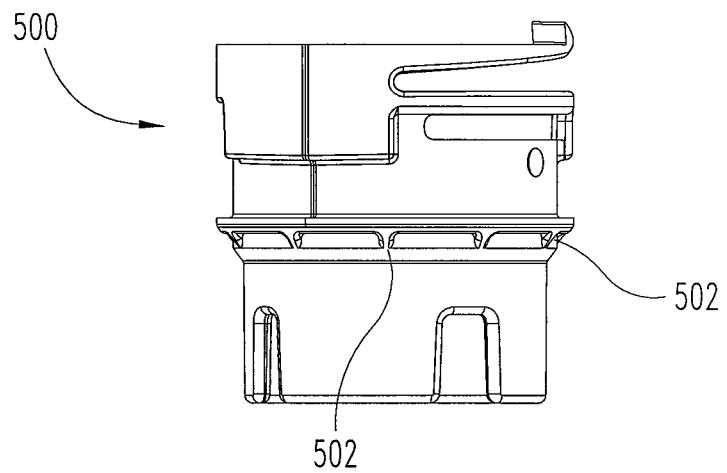
FIG. 26 is a side view of a follower shown separate from the other components of the device of FIG. 19.

Follower 500 shown in FIG. 26 includes gussets 502 around the circumference to provide a more robust part.

Figure 27A:
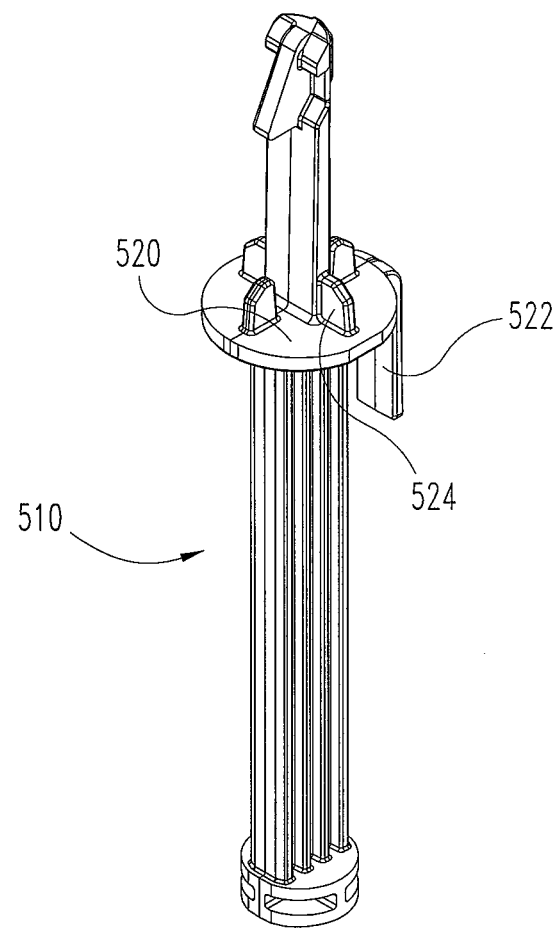
FIGS. 27a and 27b are respectively perspective and side views of a plunger element shown separate from the other components of the device of FIG. 19.
Figure 27B:
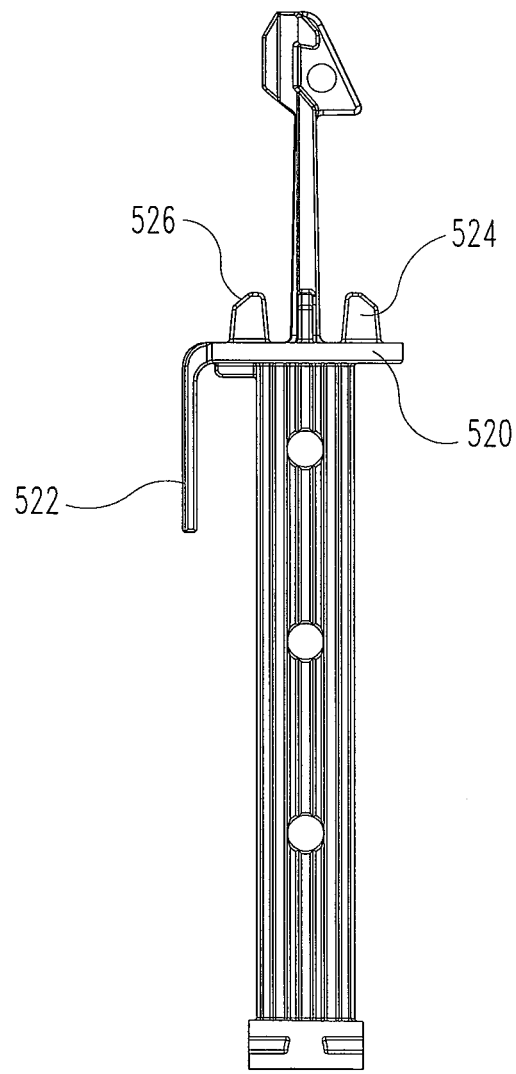

Plunger element 510 shown in FIGS. 27a and 27b is taller to allow for a larger dose. A larger diameter flange 520 has a depending bar 522 that extends farther proximally, and which has a reduced chamfer on its proximal tip. Bosses 524 are taller so as to project farther distally from flange 520, and also include chamfered outer radial peripheries 526 to facilitate assembly with the drive spring.

Devices 20 and 400 in general, and more particularly the technology claimed in this application, may be utilized in injecting a variety of medications or therapeutics into a person in need thereof. Syringes of the devices or claimed technology can be filled with any of a number of therapeutics. For example, a syringe may be filled with a myostatin antibody, an Amyloid Beta antibody, a pegylated Amyloid Beta antibody fragment, a proprotein convertase subtilisin/kexin type 9 antibody, or a calcitonin gene-related peptide antibody. The device, or claimed technology of this application, may then be operated in a manner generally as described above with respect to device 20 to inject a person with such therapeutic in the syringe.

While this invention has been shown and described as having preferred designs, the present invention may be modified within the spirit and scope of this disclosure. For example, while the biased element that the trigger assembly releases in the shown embodiment is the plunger that itself contacts the syringe piston, the inventive trigger assembly could be used to release different biased elements in alternate embodiments, or elements that are biased with parts different than coiled springs. Furthermore, the inventive trigger assembly can be used in devices having different operational principles or parts, such as with mechanisms that do not use a shuttle and in which the latching surfaces of the prongs engage, for example, an internal region of the housing or other suitably rigid part. This application is therefore intended to cover any variations, uses or adaptations of the invention using its general principles. Further, this application is intended to cover such departures from the present disclosure as come within known or customary practice in the art to which this invention pertains.

We claim:

1. A trigger assembly for an automatic injection device including a biased element and a housing, the biased element releaseable by operation of the trigger assembly for movement in a first axial direction relative to the housing, the device further including at least one latch surface and a support surface, the trigger assembly comprising:
   a button shiftable relative to the housing from a first axial position to a second axial position, said button including an actuating element extending in the first axial direction and including a radially inward face and a radially outward face, said radially inward face comprising a prong-engaging surface;
   a single prong extending from the biased element toward said button and including at least one latching surface and a button-engaging surface for sliding engagement with said prong-engaging surface of said actuating element, wherein at least one of said prong-engaging surface and said button-engaging surface is angled relative to the axial direction to provide a ramp;
   said button-engaging surface and the support surface of the device defining a radially extending opening in which said actuating element fits for said radially outward face of said actuating element to be backed up by the support surface; and
   said actuating element and said single prong structured and arranged such that when said button is in said first axial position, said at least one latching surface is in a radial position at which the at least one latch surface is engagable to prevent movement of the biased element in the first axial direction, and such that movement of said button from said first axial position to said second axial position shifts said at least one latching surface radially for disengagement from the at least one latch surface, whereby motion of said actuating element in a direction away from said prong is limited by said radially outward face of said actuating element abutting the support surface.

2. The trigger assembly of claim 1 wherein said prong includes a flexible finger and a projection therefrom on which said button-engaging surface is disposed, said flexible finger axially centered within the housing.

3. The trigger assembly of claim 1 wherein said at least one latching surface comprises first and second latching surfaces, and wherein said prong includes a flexible finger and a projection therefrom on which said button-engaging surface is disposed, said first and second latching surfaces flanking opposite sides of said projection.

4. The trigger assembly of claim 3 wherein said projection extends from a first axial height to a second axial height, said first and second latching surfaces disposed at a height between said first axial height and said second axial height.

5. The trigger assembly of claim 1 wherein said actuating element includes opposite sides in closely spaced relationship with first and second side supports of the device.

6. The trigger assembly of claim 1 wherein said button includes an end portion and a skirt that depends in the first axial direction from the end portion, wherein said actuating element is spaced from said skirt to accommodate the support surface therebetween.

7. The trigger assembly of claim 1 wherein said actuating element comprises a flange that is tapered to provide said prong-engaging surface being angled relative to the axial direction.

8. An automatic injection device comprising:
a housing;
a syringe filled with medication and including a needle, said syringe shiftable within said housing from a first position at which said needle is disposed within said housing, to a second position at which said needle projects beyond said housing;
drive means including a biased element for shifting said syringe from said first position to said second position and for forcing medication through said needle;
at least one latch surface and a support surface disposed within said housing;
a trigger assembly for triggering said drive means to allow said biased element to move in a first axial direction relative to the housing, said trigger assembly including;
a button shiftable relative to the housing from a first axial position to a second axial position, said button including an actuating element extending in the first axial direction and including a radially inward face and a radially outward face, said radially inward face comprising a prong-engaging surface;
a single prong extending from said biased element toward said button and including at least one latching surface and a button-engaging surface for sliding engagement with said prong-engaging surface of said actuating element, wherein at least one of said prong-engaging surface and said button-engaging surface is angled relative to the axial direction to provide a ramp;
said button-engaging surface and the support surface defining a radially extending opening in which said actuating element fits for said radially outward face of said actuating element to be backed up by the support surface; and said actuating element and said single prong structured and arranged such that when said button is in said first axial position, said at least one latching surface is in a radial position at which the at least one latch surface is engagable to prevent movement of the biased element in the first axial direction, and such that movement of said button from said first axial position to said second axial position shifts said at least one latching surface radially for disengagement from the at least one latch surface, whereby motion of said actuating element in a direction away from said prong is limited by said radially outward face of said actuating element abutting the support surface.

* * * * *